United States Patent
Fenn et al.

(10) Patent No.: US 12,004,754 B2
(45) Date of Patent: Jun. 11, 2024

(54) TORQUE TRANSMITTING BALL JOINT DRIVER HAVING A RIGID FIXATION MECHANISM

(71) Applicant: DePuy Synthes Products, Inc., Raynham, MA (US)

(72) Inventors: Matt Fenn, West Chester, PA (US); Jared Schoenly, West Chester, PA (US); Dave Evans, West Chester, PA (US); Michael White, Basel (CH)

(73) Assignee: DePuy Synthes Products, Inc., Raynham, MA (US)

(*) Notice: Subject to any disclaimer, the term of this patent is extended or adjusted under 35 U.S.C. 154(b) by 91 days.

(21) Appl. No.: 17/743,925

(22) Filed: May 13, 2022

(65) Prior Publication Data

US 2022/0297272 A1 Sep. 22, 2022

Related U.S. Application Data

(63) Continuation of application No. 16/207,823, filed on Dec. 3, 2018, now Pat. No. 11,331,106, which is a
(Continued)

(51) Int. Cl.
*A61B 17/70* (2006.01)
*A61B 17/16* (2006.01)
(Continued)

(52) U.S. Cl.
CPC ........ *A61B 17/162* (2013.01); *A61B 17/1757* (2013.01); *A61B 17/7076* (2013.01);
(Continued)

(58) Field of Classification Search
CPC ............ A61B 17/7076; A61B 17/7082; A61B 17/8875; A61B 17/8886; A61B 17/8888;
(Continued)

(56) References Cited

U.S. PATENT DOCUMENTS

| | | |
|---|---|---|
| 61,581 A | 1/1867 | Taylor |
| 2,526,100 A | 10/1950 | Adams |

(Continued)

FOREIGN PATENT DOCUMENTS

CH 693446 8/2003

OTHER PUBLICATIONS

International Preliminary Report on Patentability and Written Opinion, dated Jan. 22, 2015, received in connection with corresponding International Patent Application No. PCT/US2013/050338.
(Continued)

*Primary Examiner* — Samuel S Hanna
(74) *Attorney, Agent, or Firm* — BakerHostetler

(57) ABSTRACT

An articulating driver having a ball-in-socket joint. The driver may include a driver tip having a spherical head, a retention cap having a domed surface to mate with the spherical head, an input shaft, a spring disposed in an end of the input shaft and in a recess of the retention cap opposite that of the domed surface, and a housing that receives the input shaft, the spring, the retention cap and the spherical head. The housing may have a tapered end to positionally retain the spherical head therein. In another aspect, the driver may include a driver tip coupled to the input shaft that includes an interface to engage a screw. A bushing may engage the driver tip at one end and receive the screw at the other end to retain the screw within the driver.

20 Claims, 20 Drawing Sheets

Related U.S. Application Data continuation of application No. 13/547,540, filed on Jul. 12, 2012, now abandoned.

(51) Int. Cl.
| | | |
|---|---|---|
| *A61B 17/17* | (2006.01) | |
| *A61B 17/88* | (2006.01) | |
| *B25B 23/00* | (2006.01) | |
| *B25B 23/10* | (2006.01) | |
| *F16D 3/207* | (2006.01) | |

(52) U.S. Cl.
CPC ...... *A61B 17/8875* (2013.01); *B25B 23/0035* (2013.01); *B25B 23/10* (2013.01); *F16D 3/207* (2013.01); *A61B 17/7082* (2013.01)

(58) Field of Classification Search
CPC .. A61B 17/8891; B25B 23/0035; B25B 23/10
See application file for complete search history.

(56) References Cited

U.S. PATENT DOCUMENTS

| | | | |
|---|---|---|---|
| 2,526,105 A * | 10/1950 | Adams | B25B 23/0028 464/115 |
| 4,065,941 A | 1/1978 | Aoki | |
| 4,636,180 A | 1/1987 | Runkle | |
| 4,736,658 A | 4/1988 | Jore | |
| 4,807,499 A | 2/1989 | Martinez | |
| 5,007,880 A | 4/1991 | Walker | |
| 5,797,918 A | 8/1998 | McGuire et al. | |
| 6,152,826 A | 11/2000 | Profeta et al. | |
| 6,193,721 B1 | 2/2001 | Michelson | |
| 6,575,062 B2 | 6/2003 | Hahn | |
| 6,830,574 B2 | 12/2004 | Heckele et al. | |
| 6,869,366 B2 | 3/2005 | Delaney et al. | |
| 8,096,212 B2 | 1/2012 | Su | |
| 2001/0021853 A1 | 9/2001 | Heckele et al. | |
| 2004/0267275 A1 | 12/2004 | Cournoyer | |
| 2005/0015097 A1 | 1/2005 | Mujwid et al. | |
| 2005/0038432 A1 | 2/2005 | Shaolian et al. | |
| 2006/0079903 A1 | 4/2006 | Wong | |
| 2006/0200139 A1 | 9/2006 | Michelson | |
| 2006/0253120 A1* | 11/2006 | Anderson | A61B 17/8872 606/86 R |
| 2007/0093850 A1 | 4/2007 | Harris et al. | |
| 2008/0140086 A1 | 6/2008 | Moore et al. | |
| 2008/0215061 A1 | 9/2008 | Schumacher et al. | |
| 2008/0243190 A1 | 10/2008 | Dziedzic et al. | |
| 2011/0197719 A1 | 8/2011 | Neitzell et al. | |
| 2012/0265259 A1 | 10/2012 | LaPosta et al. | |
| 2013/0214496 A1* | 8/2013 | Lin | B25G 3/22 279/46.7 |

OTHER PUBLICATIONS

International Search Report and Written Opinion, dated May 12, 2014, received in connection with corresponding International Patent Application No. PCT/US2013/050338.

* cited by examiner

SECTION A-A

SECTION A-A

SECTION D-D

SECTION B-B

SECTION A-A

SECTION A-A

TORQUE TRANSMITTING BALL JOINT DRIVER HAVING A RIGID FIXATION MECHANISM

CROSS REFERENCE TO RELATED APPLICATIONS

This application is a continuation of U.S. patent application Ser. No. 16/207,823, filed Dec. 3, 2018, now U.S. Pat. No. 11,331,106, issued May 17, 2022. U.S. patent application Ser. No. 16/207,823 is a continuation of U.S. patent application Ser. No. 13/547,450, filed Jul. 12, 2012. Each of the aforementioned applications is incorporated by reference in its entirety for all purposes.

BACKGROUND

In procedures such as an anterior lumbar interbody fusion (ALIF), lateral lumbar interbody fusion (XLIF), cervical spine surgery, etc., when a disc space has been cleared out, a metal, polymer, or bone spacer is typically implanted between the two adjoining vertebrae. After these spacers or "cages" are inserted, surgeons often use metal screws, plates, and/or rods to further stabilize the spine. To insert the screws, a driver device having an articulating driver head may be used to deliver the screws to their spinal column and lock them into place.

In such a driver device, a u-joint may be provided to allow the driver head to articulate with respect to an input shaft. However, the u-joint may have a range of angulation that makes it difficult for a user to maintain an appropriate force on a component (e.g., a screw) being driven. Further, in some drivers, a bushing within the driver head that retains a driver tip may wear out over time, which causes the driver tip to move around, thus making it difficult for the user to drive the component.

SUMMARY

The present disclosure provides an articulating driver and for a ball-in-socket joint. The driver may include a driver tip having a spherical head, a retention cap having a domed surface to mate with the spherical head, an input shaft, a spring disposed in an end of the input shaft and in a recess of the retention cap opposite that of the domed surface, and a housing that receives the input shaft, the spring, the retention cap and the spherical head. The housing may have a tapered end to positionally retain the spherical head therein. In accordance with an aspect, the spherical head has a plurality of grooves defined in a surface thereof and the housing defines a plurality of holes. Each of the holes may receive a pin that passes through the housing and is received within a respective groove of the spherical head.

In accordance with some implementations, there is provided a ball-in-socket joint that includes an input shaft, a output shaft having a spherical head, the spherical head having a plurality of grooves defined therein, a retention cap having a domed surface to mate with the spherical head, a spring disposed in an end of the input shaft and in a recess of the retention cap opposite that of the domed surface, and a housing that defines a plurality of holes and receives the input shaft, the spring, the retention cap and the spherical head, The housing may have a tapered end to positionally retain the spherical head therein. Each of the holes may receive a pin that passes through the housing and is received within a respective groove of the spherical head.

In accordance with some implementations, there is provided a ball-in-socket joint that includes a housing that defines a plurality of holes, where the housing is tapered at one end. The ball-in-socket joint also may also include an input shaft, a spring disposed in an end of the input shaft that is disposed within the housing, a retention cap disposed with the house that receives the spring at one end and has a domed surface at the other end thereof, and an output shaft having a spherical head that is disposed within the housing. The ball shaped head may have defined therein a plurality of grooves within which pins inserted into the holes or inward protrusions cooperate to transmit torque from the input shaft to the output shaft.

In accordance with some implementations, there is provided a driver having an input shaft adapted to transmit torque and a driver tip coupled to the input shaft. The driver tip may include an interface defined at an end thereof adapted to engage a screw. The driver may also include a bushing that engages the driver tip at one end and that receives the screw at the other end. The screw may be received within the bushing to engage the interface, and the input shaft is adapted to apply torque to the screw through the interface and to apply torque to the bushing by the engagement of the bushing with the driver tip.

In accordance with some implementations, there is provided a method of engaging a screw with a driver having an input shaft, a bushing, and a driver tip. The method may include engaging the bushing with the driver tip; advancing the bushing along a longitudinal axis of the driver tip in a first direction to expose a screw interface; receiving the screw at the screw interface; and moving the bushing in a second direction along the longitudinal axis to couple a head of the screw with the bushing to retain the screw within the driver.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The foregoing summary, as well as the following detailed description of illustrative embodiments, is better understood when read in conjunction with the appended drawings. For the purpose of illustrating the embodiments, there are shown in the drawings example constructions of the embodiments; however, the embodiments are not limited to the specific methods and instrumentalities disclosed. In the drawings.

DETAILED DESCRIPTION

With references to the FIGS., there is illustrated an articulating driver 100 and a ball-in-socket joint 102. As will be described herein, the ball-in-socket joint 102 allows a driver tip 126 or other output shaft to articulate while transmitting input torque from an input shaft 104 to the driver tip 126. The input torque turns e.g., a screw or other component being driven by the articulating driver 100. The articulating driver 100 may be a jointed awl, screw driver or drill.

Figure 1A:
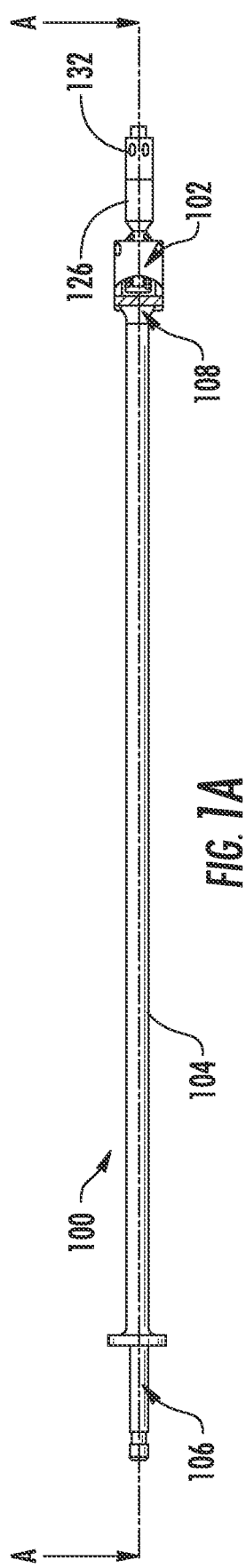
FIG. 1A illustrates a driver device having an articulating driver head.
Figure 1B:
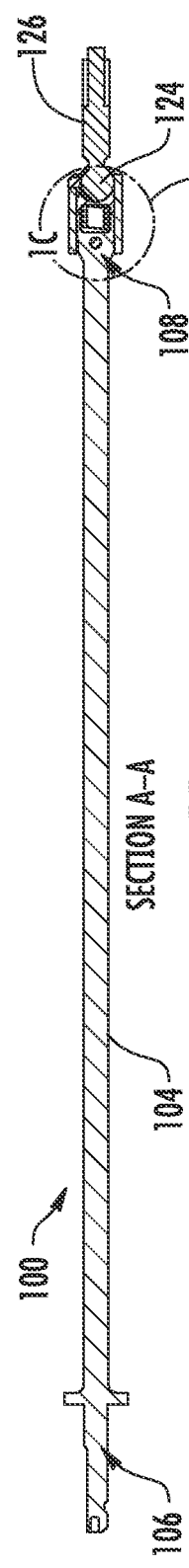
FIG. 1B illustrates a sectional view of the driver device along section line A-A of FIG. 1A.
Figure 1C:
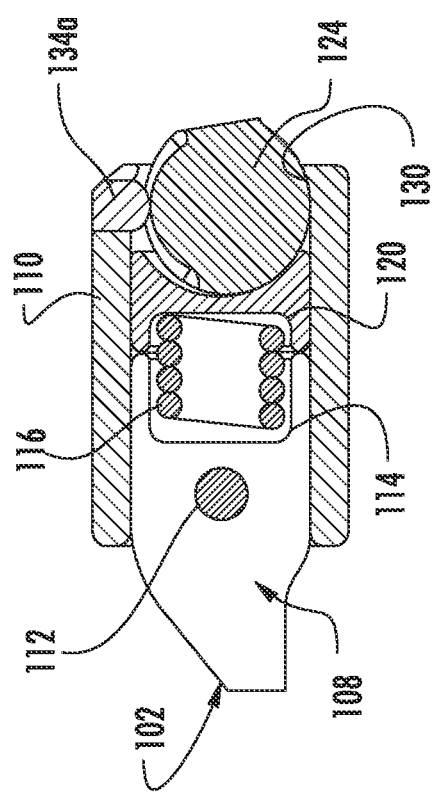
FIG. 1C illustrates a ball-in-socket joint of the driver devices of FIG. 1A in greater detail.
Figure 2:
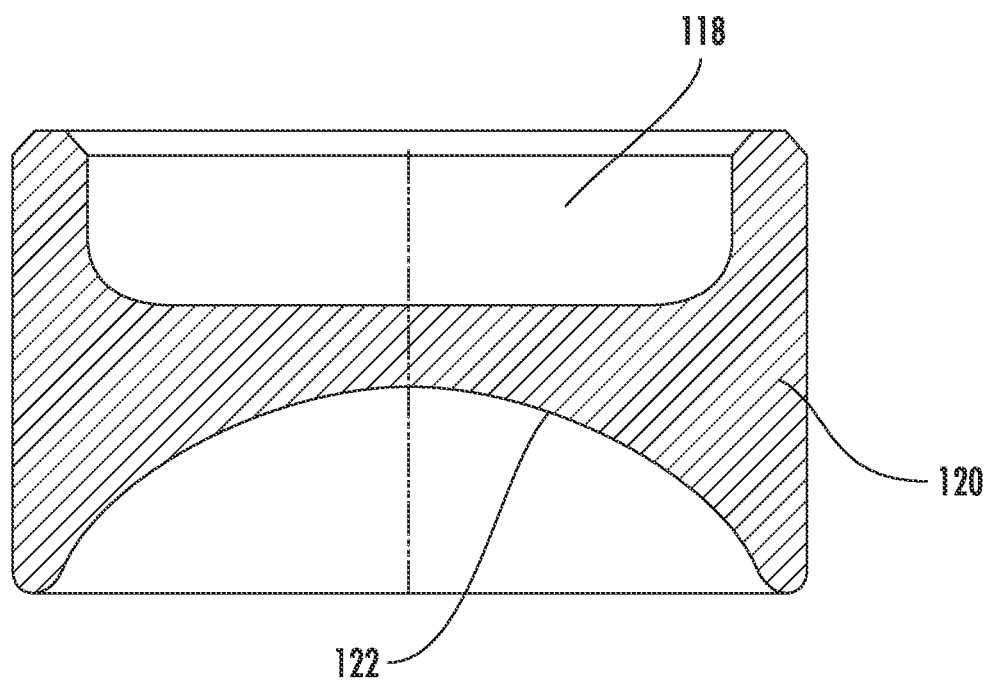
FIG. 2 illustrates a retention cap of FIGS. 1A-1C.

As shown in FIGS. 1A-1C, the articulating driver 100 consists of the input shaft 104 that, at a first end 106, connects to a handle (not shown) and at a second end 108 connects to an articulation housing assembly 110 that forms an outer portion of the ball-in-socket joint 102. The input shaft 104 may be any type of shaft capable of transmitting input torque from the handle or a power tool to which the input shaft 104 is attached. At the second end 108 of the input shaft 104, a cavity 114 is defined that accepts a spring 116 or the cavity walls are composed of a spring. One end of the spring 116 is received within the cavity 114, and the other end of the spring 116 is received within a recess 118 of a retention cap 120, which is shown in greater detail in FIG. 2. As will be described later, the spring 116 provides positional retention of the driver tip 126. The retention cap 120 transmits force from the spring 116 to a spherical head 124 of the driver tip 126 that is secured between the retention cap 120 and a tapered inner surface 130 of the articulation housing assembly 110. As shown in FIG. 2, a domed surface 122 may be defined at an end of the retention cap 120 opposite the recess 118 to receive the spherical head 124.

As shown in FIG. 1C, the articulation housing assembly 110 receives the second end 108 of the input shaft 104, the spring 116, the retention cap 120, and the spherical head 124 of the driver tip 126. As shown in FIG. 4, the articulation housing assembly 110 defines holes 136 within which pins 134a, 134b and 134c are pressed. The pins 134a, 134b and 134c are received within grooves 128a, 128b and 128c of the spherical head 124 (see, FIGS. 3A-3D). Through the cooperation of the pins 134a, 134b and 134c and the grooves 128a, 128b and 128c, the spherical head 124 transmits torque to an attachment that is received within a bushing 132 (see, FIG. 1A). The bushing 132 provides positional retention of the attachment and may be made from Polyether ether ketone (PEEK) or an appropriate plastic or metal.

In accordance with aspects of the present disclosure, the domed surface 122 of the retention cap 120 and the tapered inner surface 130 of the articulation housing assembly 110 may each have a radius that is similar to, and designed to interface with the spherical head 124 head of the driver tip 126. These radii allow the driver tip 126 to articulate within the articulation housing assembly 110, while retaining the spherical head 124 within the articulation housing assembly 110. Thus, the interaction of the spring 116 pressing on the retention cap 120, which mates to the spherical head 124, and the tapered inner surface 130 of the articulation housing assembly 110 serve to positionally retain the driver tip 126 within the articulation housing assembly 110.

Figure 3A:
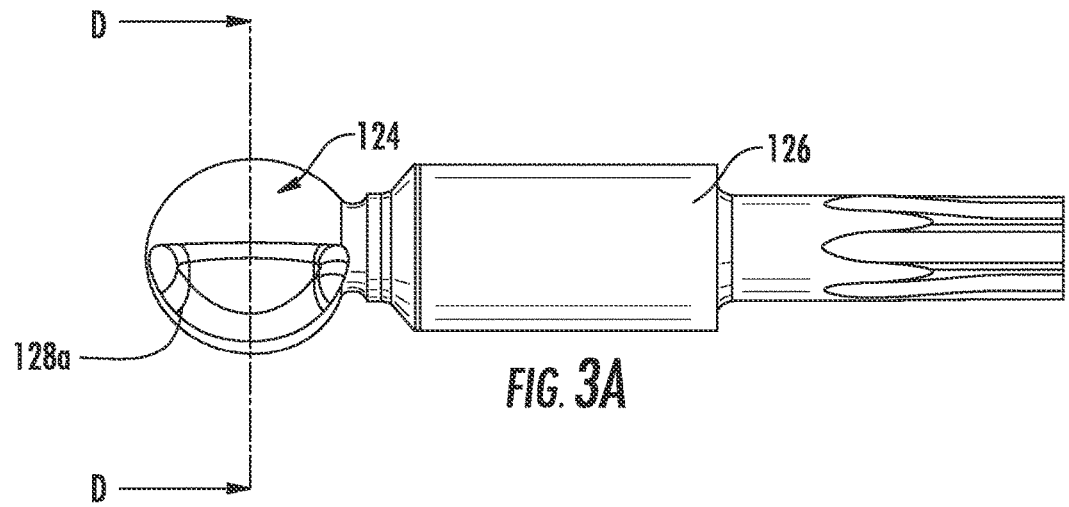
FIGS. 3A-3B illustrate a spherical head of FIGS. 1A-1C in greater detail.
Figure 3B:
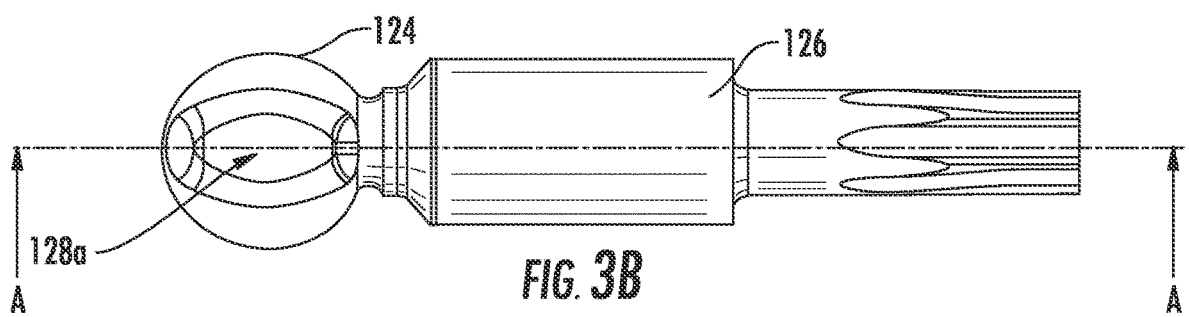
Figure 3C:
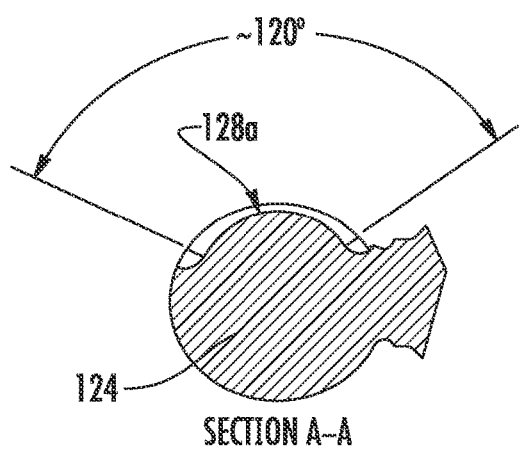
FIG. 3C illustrates a sectional view of the spherical head along section line A-A of FIG. 3B.
Figure 3D:
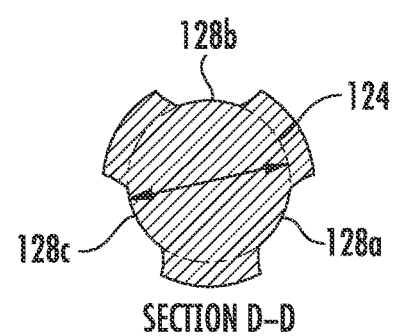
FIG. 3D illustrates a sectional view of the spherical head along section line D-D of FIG. 3A.
Figure 4A:
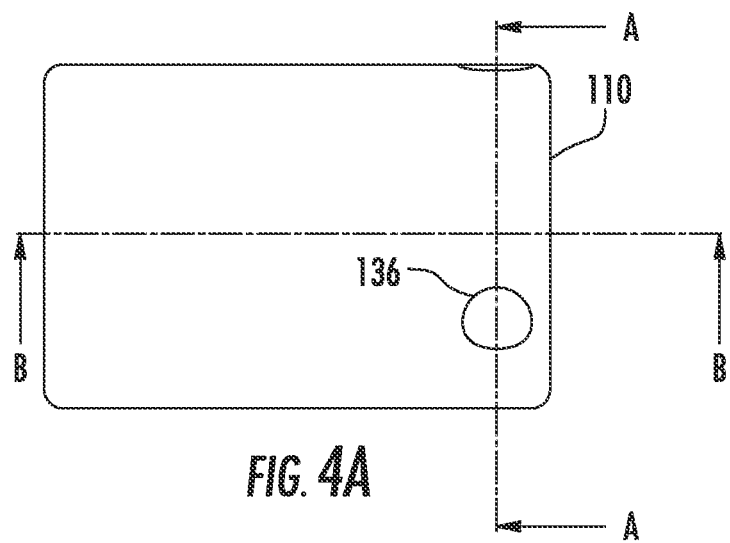
FIG. 4A illustrates an articulation housing assembly of FIGS. 1A-1C in greater detail.
Figure 4B:
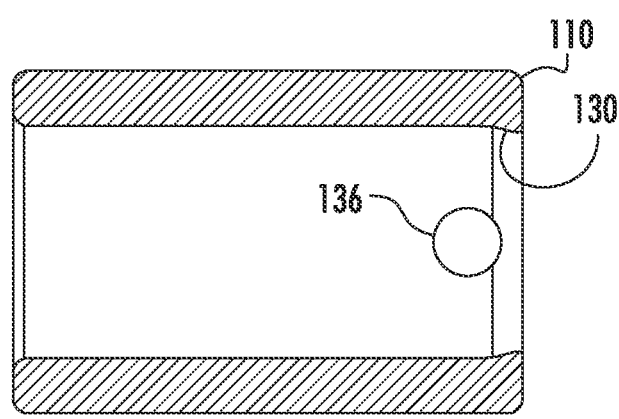
FIG. 4B illustrates a sectional view of the articulation housing assembly along section line B-B of FIG. 4A.
Figure 4C:
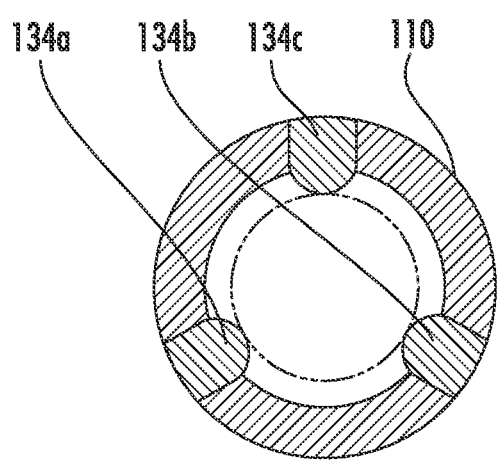
FIG. 4C illustrates a sectional view of the articulation housing assembly along section line A-A of FIG. 4A.

FIGS. 3A-3D illustrate the spherical head 124 and the driver tip 126 in greater detail. As shown in FIG. 3A, the grooves 128a, 128b and 128c form a generally ovular shape on the surface of the spherical head 124, and are wider near the diameter and taper moving toward the circumference. The grooves 128a, 128b and 128c are formed having generally having a W-shape cross-section (see, FIG. 3D) within spherical head 124. In some implementations, the grooves 128a, 128b and 128c may be milled into spherical head portion at offsets of 120°. As shown in FIG. 3C, the grooves may extend over an approximately 120° arc across the surface of the spherical head 124. Thus, it can be appreciated that the shape of the grooves 128a, 128b and 128c maybe any shape such that the grooves cooperate with the pins 134a, 134b and 134c provide approximately 45-50° of angulation of the driver tip 126 with respect to the input shaft 104 over a 360° rotation.

During assembly, the input shaft 104 is pressed in the articulation housing assembly 110 and cross-pinned to the articulation housing assembly 110 using a pin 112. The pin 112 may be pressed-in and retained by an interference fit with the shaft 104; the pin 112 may be welded in place, or may be threaded into the shaft 104 or retained within a further sleeve used to prevent pins 112, 134a-134c from backing out. Other attachment mechanisms may be used in place of the pin 112.

The various components above may be made from stainless steel, titanium, titanium alloy, ceramic, etc. The retention cap 120 may be fabricated from PEEK, stainless steel, polyethylene, or any metallic or polymetric material. The retention cap 120 may also include a TiN coating to limit wear and galling on the spherical head 124.

In some implementations, the various components of the driver 100 may have the following dimensions. The radius of curvature of the domed surface 122 may be approximately 3.6 mm and may have a depth of 1.8 mm. The spherical head 124 portion may have a diameter approximately 6.5 mm. The recess 118 may have a depth of 1.5 mm to receive a portion of the spring 116. The retention cap 120 may have a total height of 3.0 mm. The articulation housing assembly may have a length of 15 mm and the tapered inner surface may begin 1.6 mm from the edge of the housing assembly. The inner diameter of the articulation housing assembly may be 7.1 mm. The cavity defined in the second end of the input shaft may have a depth of 3.5 mm.

During operation, as the user rotates the input shaft 104, torque is transmitted to the articulation housing assembly 110 via the press-fit and the pin 112. This torque is then transmitted from the articulation housing assembly 110 to the driver tip via action of the pins 134a, 134b and 134c are received within the grooves 128a, 128b and 128c of the spherical head 124 of the driver tip 126. The driver tip 126 then transmits the torque to the attachment to turn, e.g., screws for insertion into bone.

Thus, the ball-in-socket joint 102 of the present disclosure can be positioned stably in a multi-angle screwing/unscrewing operation. In particular, because the ball-in-socket joint 102 provides for approximately 45-50° of angulation, the driver 100 maintains the driver tip 126 within a useful range of operation.

Referring now to FIGS. 5-8, the engagement of a screw with the articulating driver 100 will be described. As shown in detail in exploded view of FIG. 5, a bushing 232 includes inner threads 506 disposed at a distal end thereof and inner threads 508 disposed at the proximal end thereof. The diameter of the inner threads 506 and inner threads 508 have a dimension that is complementary with an outer threaded portion 514 of the screw 502 and a threaded region 510 of the driver tip 126, respectively. The pitches of the inner threads 506 and outer threaded portion 514, and inner threads 508 and a threaded region 510 may be respectively optimized to match. The outer threaded portion 514 may be a conical thread or a straight thread. In some implementations, the diameter of the inner threads 506 may be larger than the inner threads 508 to allow the inner threads 506 to pass over the threaded region 510, as will be described below. In some implementations, the diameter of the inner threads 506 and the outer threads 508 may be the same.

The bushing further includes a stop region 516, which cooperates with an aiming device or guide to halt forward progress of the bushing 232 within the aiming device when the screw 502 is driven by the articulating driver 100. Further details of the interaction of the stop region 516 and the aiming device will be described below with reference to FIGS. 9-12. Also as shown, the driver tip 126 includes at a distal end thereof a screw interface 512 that is adapted to engage a complementary recess defined within the head the screw 502. The screw interface 512 and complementary recess may be star-shaped, hexagonal, square, a polygonal shape, etc.

Figure 5:
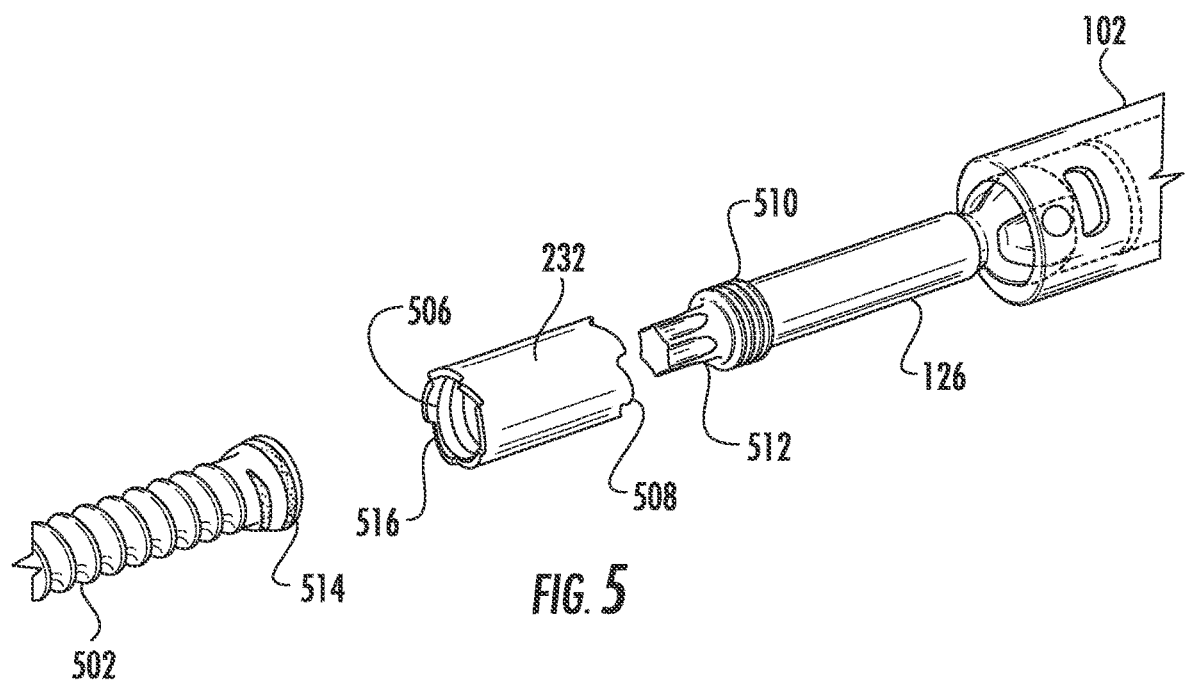
FIGS. 5-8 illustrate an engagement of a screw with a driver device such as that shown in FIG. 1.
Figure 6:
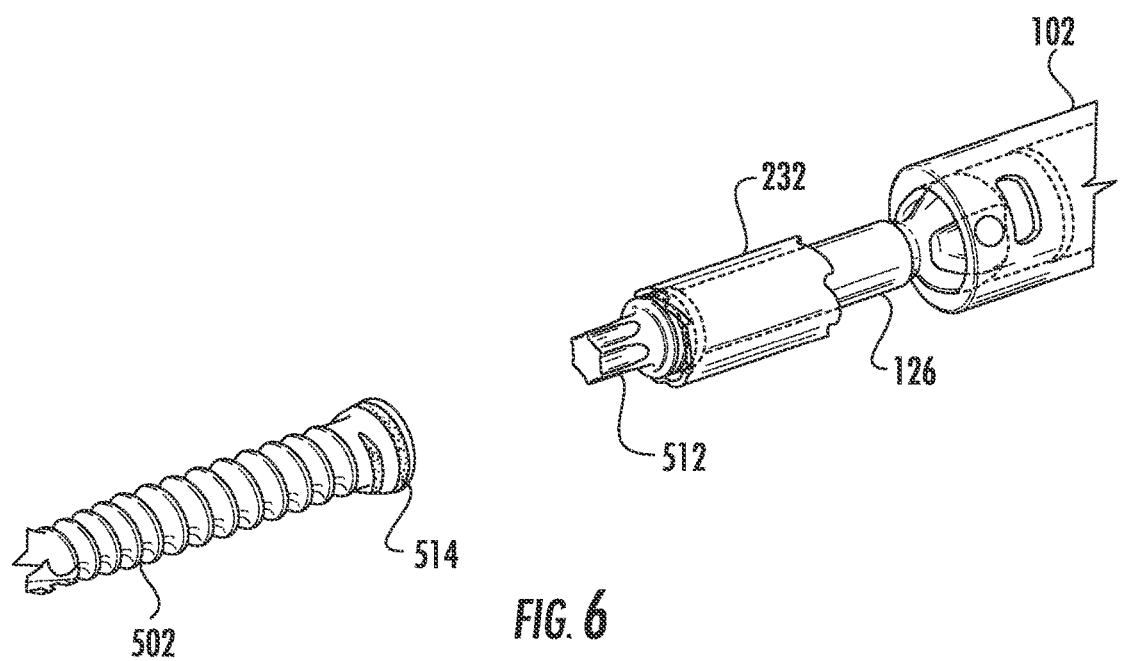

The operational engagement of the bushing 232, the driver tip 126 and the screw 502 will now be described. FIG. 5 illustrates the components in a separated state, where initially, the bushing 232 is placed over the screw interface 512 to engage the inner threads 508 with the threaded region 510. The bushing 232 is rotated in, e.g., a clockwise direction such that the inner threads 508 mesh with the threaded region 510 to advance the bushing in the proximal direction. As shown in FIG. 6, the bushing 232 may be moved in the proximal direction such that the inner threads 506 pass over the threaded region 510, as the diameter of the inner threads 506 may be larger than the threaded region 510. In implementations where the diameter of the inner threads 506 is equal to inner threads 508, the inner threads may engage the threaded region 510. As such, an intermediate state of engagement is achieved (shown in FIG. 6) where the screw interface 512 and a portion of the threaded region 510 protrude through the distal end of the bushing 232. Thus, the screw interface 512 is positioned such that it can be received within a complementary recess in the head of the screw 502.

Figure 7:
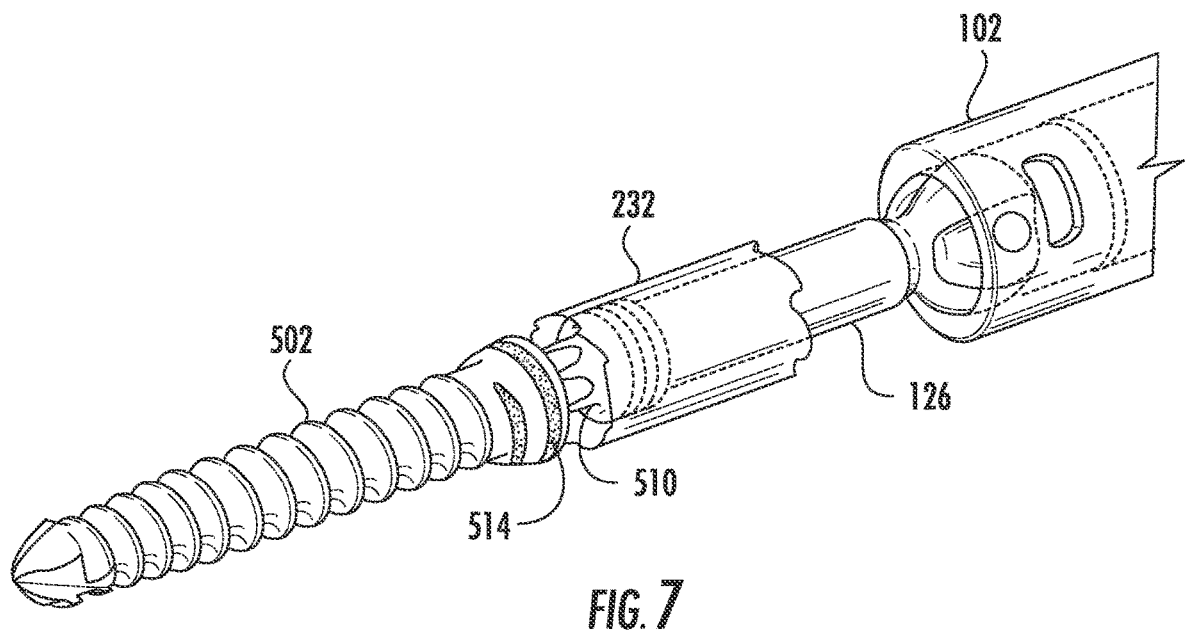

Next, as shown in FIG. 7, the screw 502 is brought into proximity with the screw interface 512 such that the interface may engage the head of the screw 502. An operator may then rotate the bushing 232 in e.g., the counterclockwise direction to cause the inner threads 508 to mesh with the threaded region 510, thus moving the bushing 232 in the distal direction.

Figure 8:
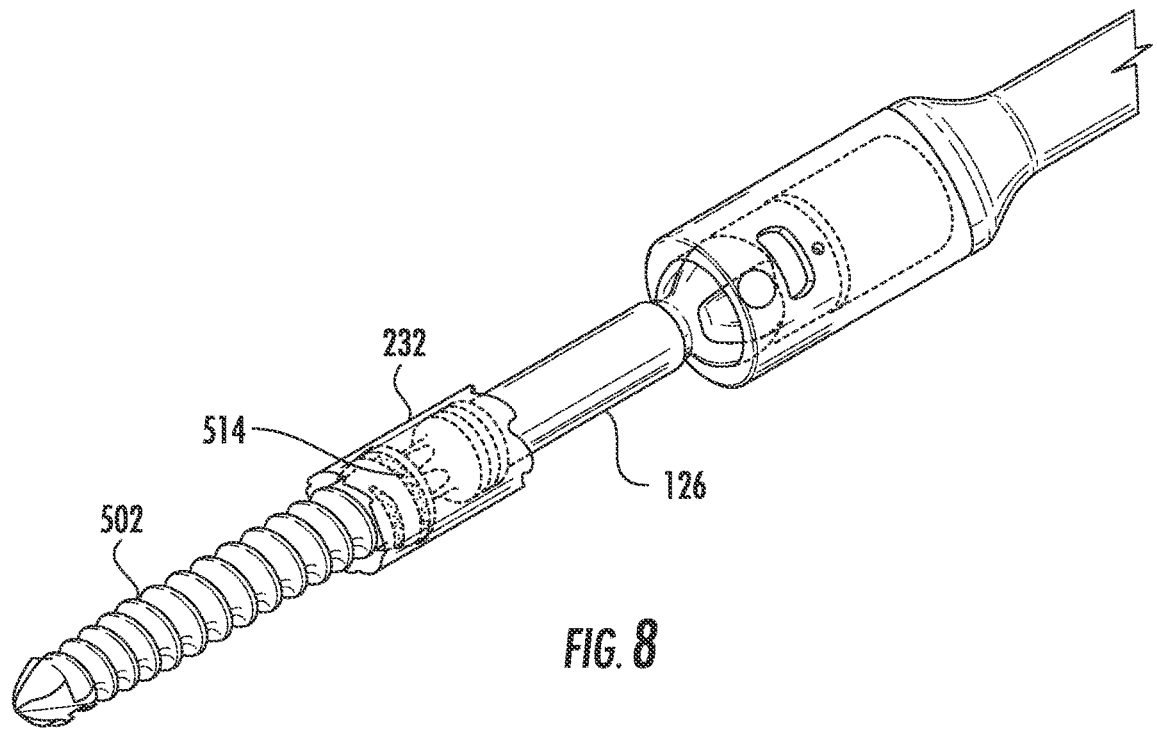
Figure 9:
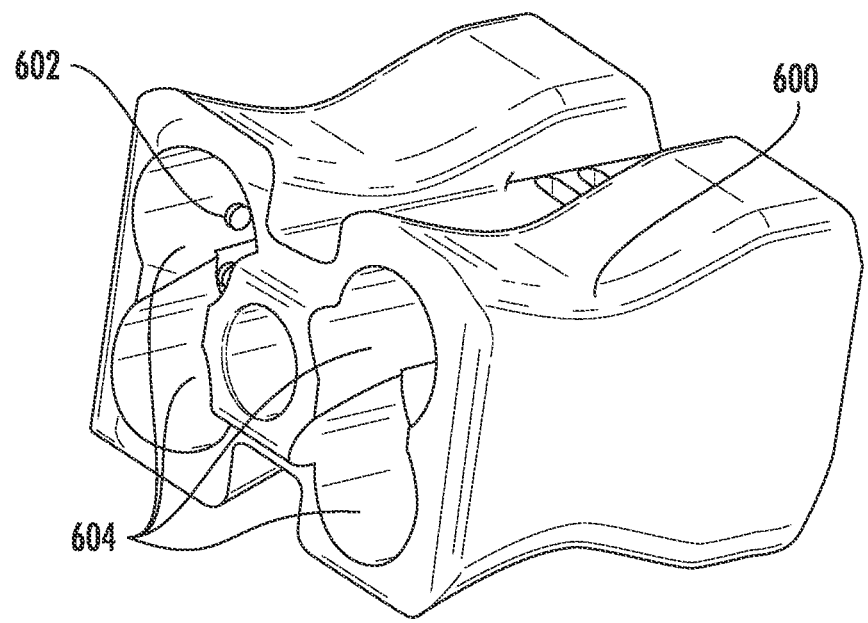
FIGS. 9-12 illustrate an interaction of a stop region of a bushing of the driver device and an aiming device to provide disengagement of the screw from the driver device according to an embodiment.
Figure 10:
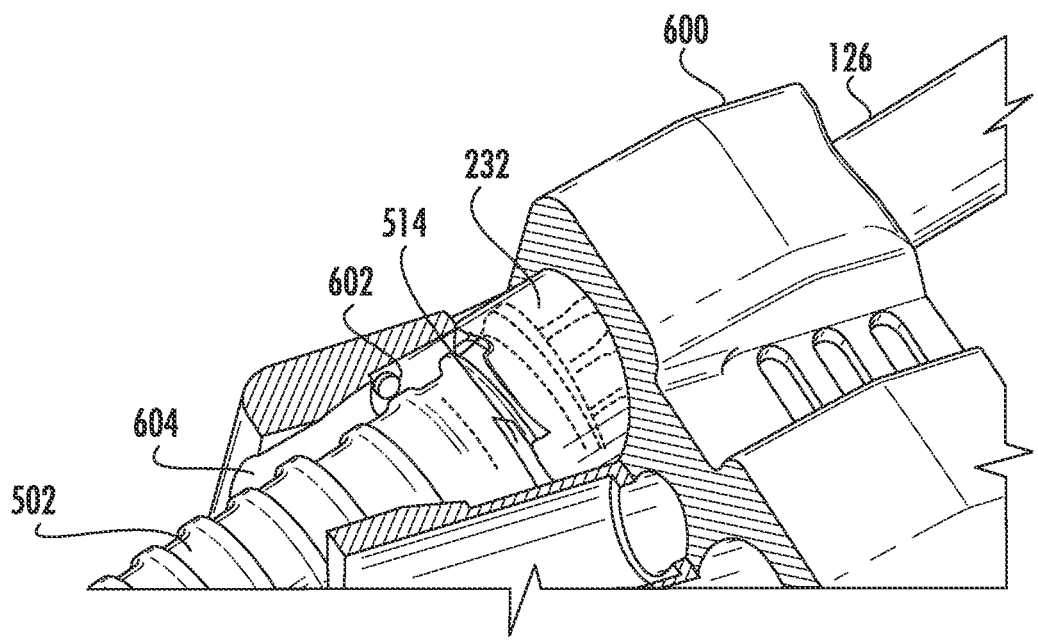

As shown in fully engaged view of FIG. 8, the bushing 232 is moved distally until the inner threads 506 engage the threaded portion 514 of the screw 502. The engagement of the inner threads 506 and the threaded portion 514 serves to retain the screw 502 within the bushing 232. Thus, FIG. 8 illustrates the screw 502 when loaded into the articulating driver 100 and ready to be driven into an associated plate or portion of bone.

With reference to FIGS. 9-12, the operation of the articulating driver 100 to drive the screw 502 into an associated plate or portion of bone will now be described. As shown in FIGS. 9-12, an aiming device or guide 600 may be used to guide the screw 502. The aiming device 600 includes a plurality of aiming holes 604, each having a pin 602 that protrudes through an inner wall thereof at a distal end. An operator may drive the screw 502 into, e.g., bone, by inserting the screw 502 into an appropriate one of the aiming holes 604. The screw 502 will pass through the aiming hole 604 and out of the aiming device 600. However, the aiming device 600 is sized such that the bushing 232 remains rotably positioned within a proximal portion of the aiming hole 604 (see, e.g., FIG. 10). As the operator drives the screw 502 using the driver 100, the screw 502 and bushing 232 will rotate and move distally within the aiming hole 604 as the screw 502 engages the plate or bone.

Figure 11:
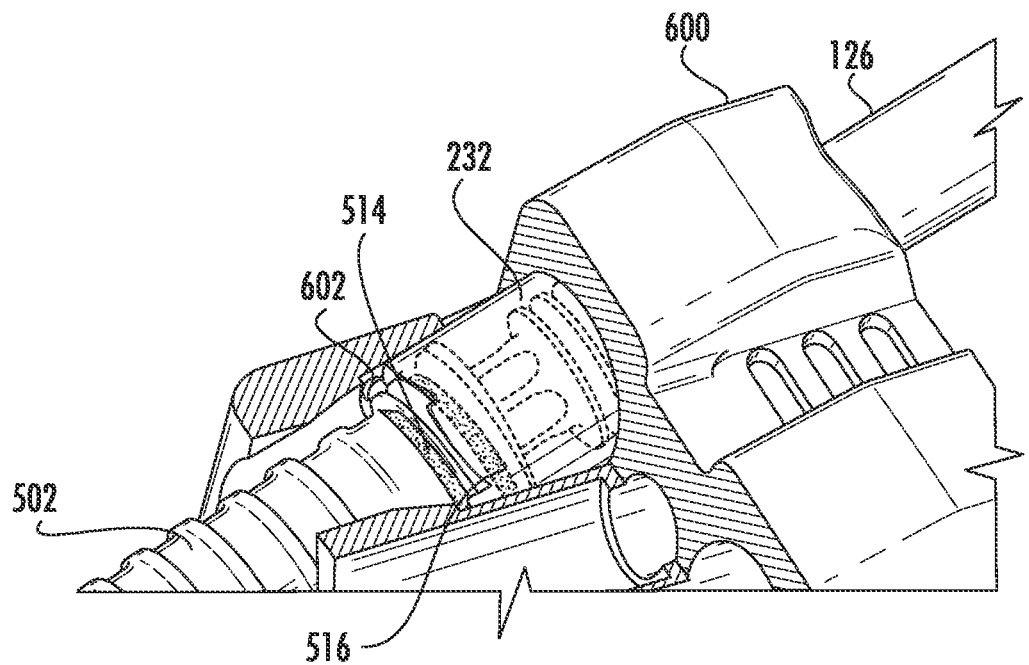

As shown in FIG. 11, the distal movement will cause the stop region 516 of the bushing 232 to engage the pin 602. As illustrated in FIGS. 5 and 11, the stop region 516 may be formed having a jagged or zig-zag edge, such that the pin 602 is caught within a vertex 516a formed by the edge. Engagement of the stop region 516 with the pin 602 will cause the bushing 232 to cease rotational and longitudinal movement (i.e., it will be stopped within the aiming hole 604). It is noted that other designs may be used to stop the advancement of the bushing 232 within the aiming hole 604 (e.g., frictional engagement).

Figure 12:
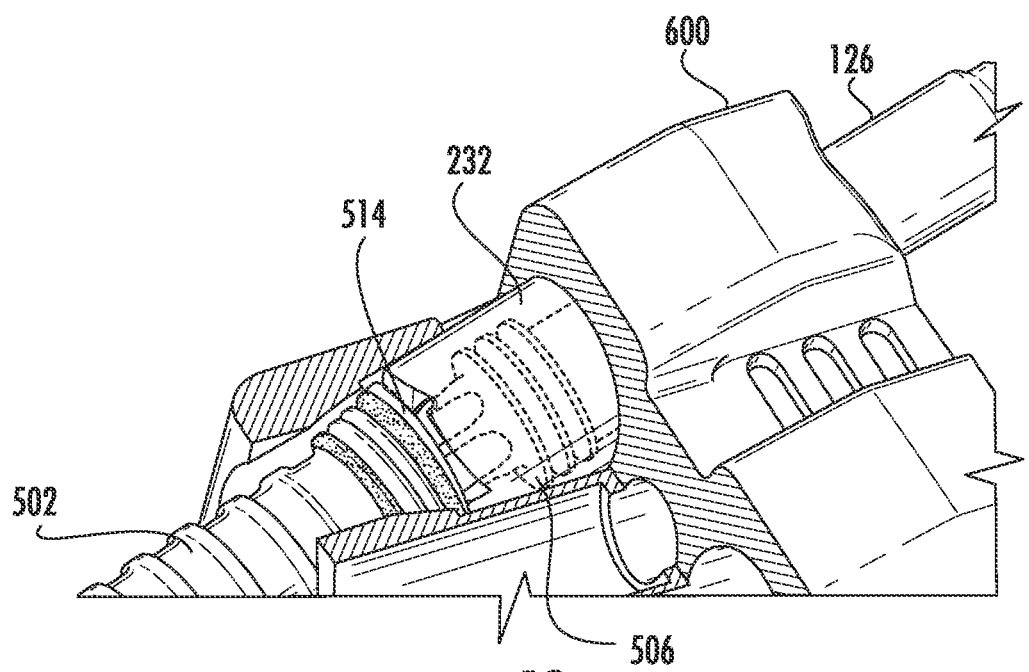

After the bushing 232 is stopped, the application of torque to the driver tip 126 will continue to rotate the screw 502 within the bushing 232. Thus, the screw 502 will continue to be driven in the distal direction along the longitudinal axis of the driver tip 126. As shown in FIG. 12, continuing to drive the screw 502 will rotate the threaded region 514 within the inner threads 506, causing the threaded region 514 to progress out of the distal end of the bushing 232. As such, the screw 502 advances from the bushing 232 and will be released from the driver 100. Operation of the articulating driver 100 may continue in order to drive the screw 502 into its final position through the continued engagement of the screw interface 512 with the head of the screw 502. Once the screw 502 reaches its final position, the articulating driver 100 may be withdrawn from the aiming device or guide 600.

Referring now to FIGS. 13-20, the engagement of a screw with the articulating driver 100 will be described in accordance with another implementation. Many of the details of the articulating driver 100 of this implementation are the same as the that described with reference to FIGS. 1-12; however, as shown in detail in FIGS. 13 and 14, a bushing 732 includes inner threads 706 (FIG. 14) disposed at a distal end thereof and inner threads 708 disposed at the proximal end thereof. The diameter of the inner threads 706 and inner threads 708 have a dimension that is complementary with an outer threaded portion 514 of the screw 502 and a threaded region 510 of the driver tip 126, respectively. The pitches of the inner threads 706 and outer threaded portion 514, and inner threads 708 and a threaded region 510 may be respectively optimized to match. The outer threaded portion 514 may be a conical thread or a straight thread. In some implementations, the diameter of the inner threads 706 may be larger than the inner threads 708 to allow the inner threads 706 to pass over the threaded region 510, as will be described below. In some implementations, the diameter of the inner threads 706 and the outer threads 708 may be the same.

The bushing 732 further includes lobes 734, which cooperate with an aiming device or guide to halt forward progress of the bushing 732 within the aiming device when the screw 502 is driven by the articulating driver 100. The cooperation of the lobes 734 with the aiming device is described below in more detail with reference to FIGS. 17-20. The lobes 734 may be formed such that they extend outwardly from the circumference of the bushing 732. Three or four lobes 734 may be provided at the proximal end of the bushing 732; however any number of lobes may be provided.

Figure 14:
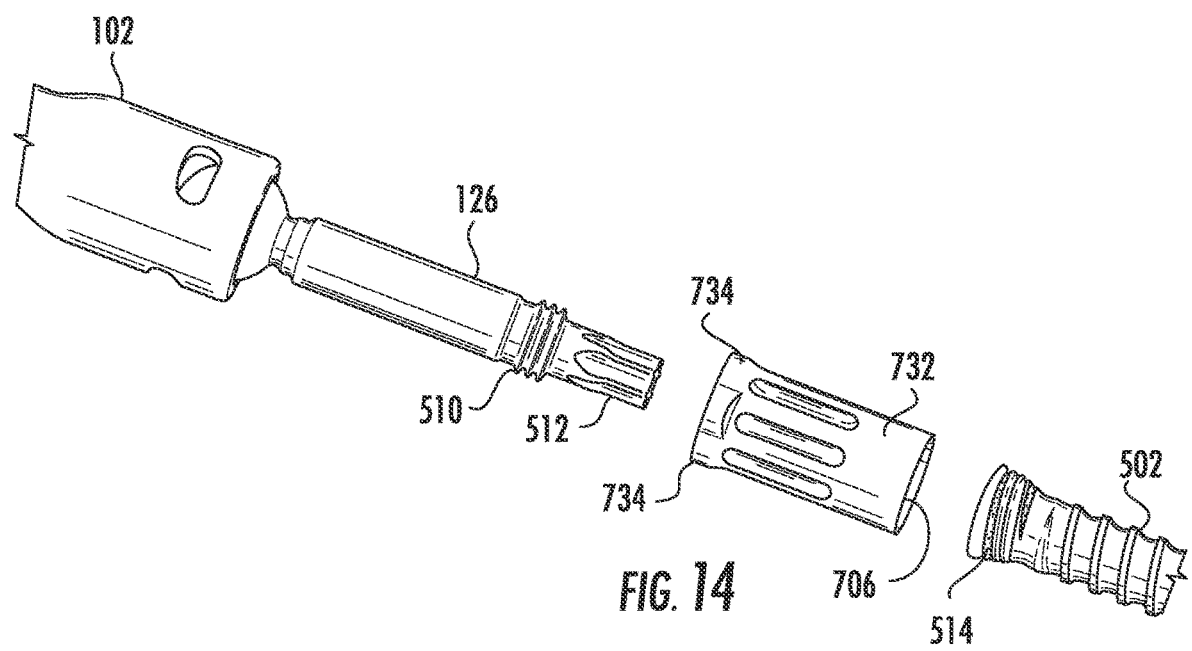
Figure 15:
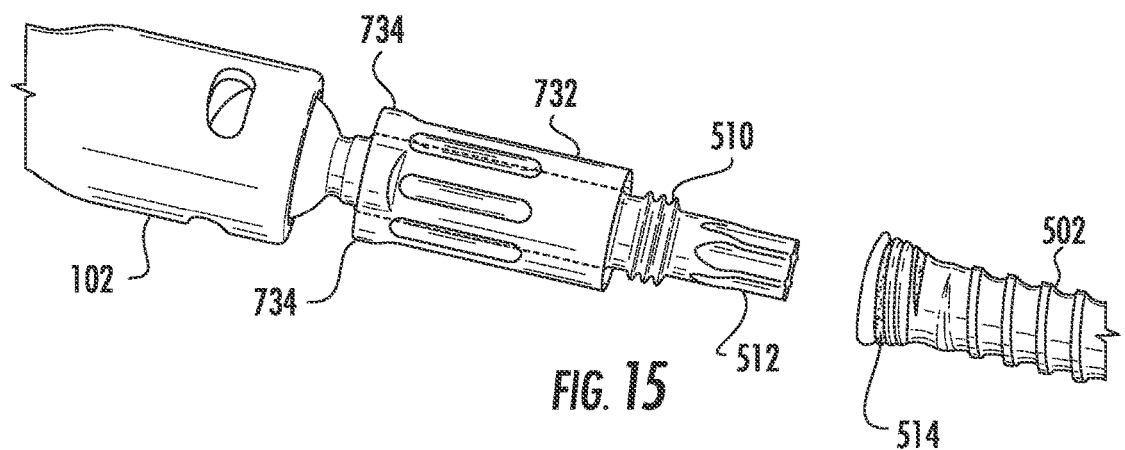

The operational engagement of the bushing 732, the driver tip 126 and the screw 502 will now be described. FIG. 14 illustrates the components in a separated state, where initially, the bushing 732 is placed over the screw interface 512 to engage the inner threads 508 with the threaded region 510. The bushing 732 is rotated in, e.g., a clockwise direction such that the inner threads 508 mesh with the threaded region 510 to advance the bushing in the proximal direction. As shown in FIG. 15, the bushing 732 may be moved in the proximal direction such that the inner threads 506 pass over the threaded region 510, as the diameter of the inner threads 506 may be larger than the threaded region 510. In implementations where the diameter of the inner threads 506 is equal to inner threads 508, the inner threads may engage the threaded region 510. As such, an intermediate state of engagement is achieved (shown in FIG. 15) where the screw interface 512 and a portion of the threaded region 510 protrude through the distal end of the bushing 232. Thus, the screw interface 512 is positioned such that it can be received within a complementary recess in the head of the screw 502.

Figure 16:
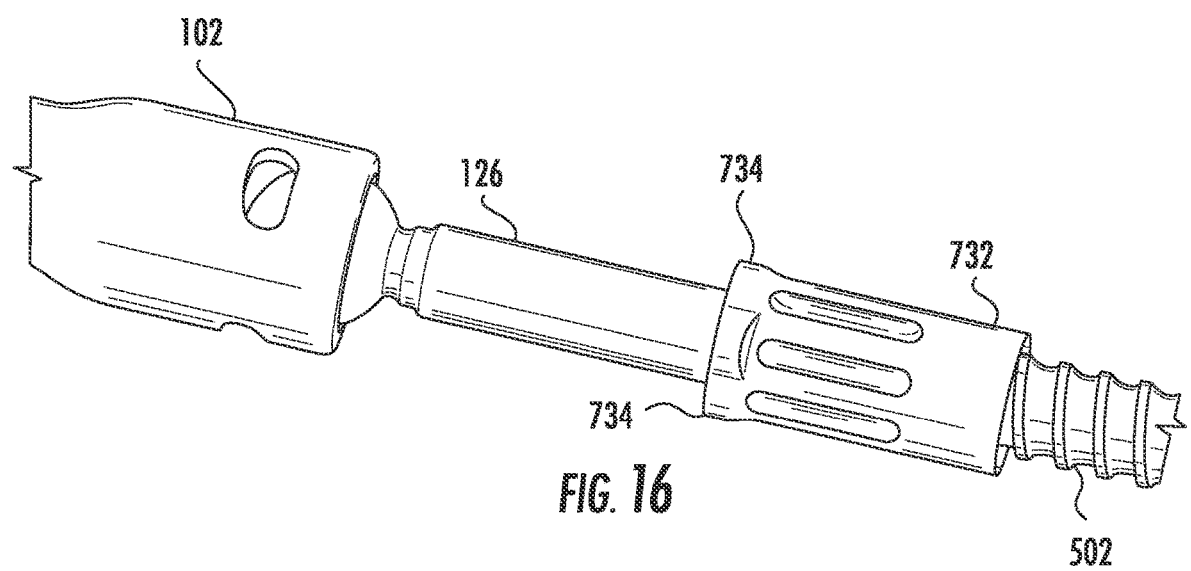

Next, as shown in fully engaged view of FIG. 16, the bushing 732 is moved distally until the inner threads 506 engage the threaded portion 514 of the screw 502. The engagement of the inner threads 506 and the threaded portion 514 serves to retain the screw 502 within the bushing 732. Thus, FIG. 16 illustrates the screw 502 when loaded into the articulating driver 100 and ready to be driven into an associated plate or portion of bone.

With reference to FIGS. 17-20, the operation of the articulating driver 100 to drive the screw 502 into an associated plate or portion of bone will now be described. As shown in FIGS. 17-20, an aiming device or guide 800 may be used to guide the screw 502. The aiming device 800 includes a plurality of aiming holes 804, each having circumferential lobes 802 at a proximal end. The circumferential lobes 802 may extend inwardly from a center of each aiming hole 804 and receive the lobes 734 of the bushing 732. An operator may drive the screw 502 into, e.g., bone, by inserting the screw 502 into an appropriate one of the aiming holes 804. The screw 502 will pass through the aiming hole 804 and out of the aiming device 800. However, the aiming device 800 is sized such that the bushing 732 remains rotably positioned within a proximal portion of the aiming hole 804 (see, e.g., FIG. 18). As the operator drives the screw 502 using the driver 100, the screw 502 and bushing 732 will rotate and move distally within the aiming hole 804 as the screw 502 engages the plate or bone.

Figure 13:
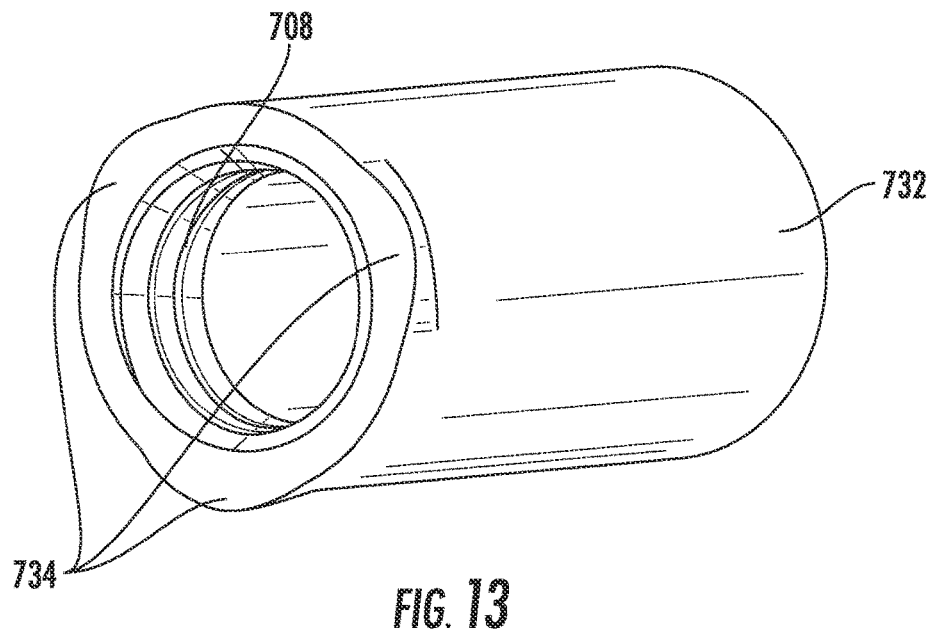
FIGS. 13-20 illustrate an interaction of a stop region of a bushing of the driver device and an aiming device to provide tapered disengagement of the screw from the driver device in accordance with another embodiment.
Figure 17:
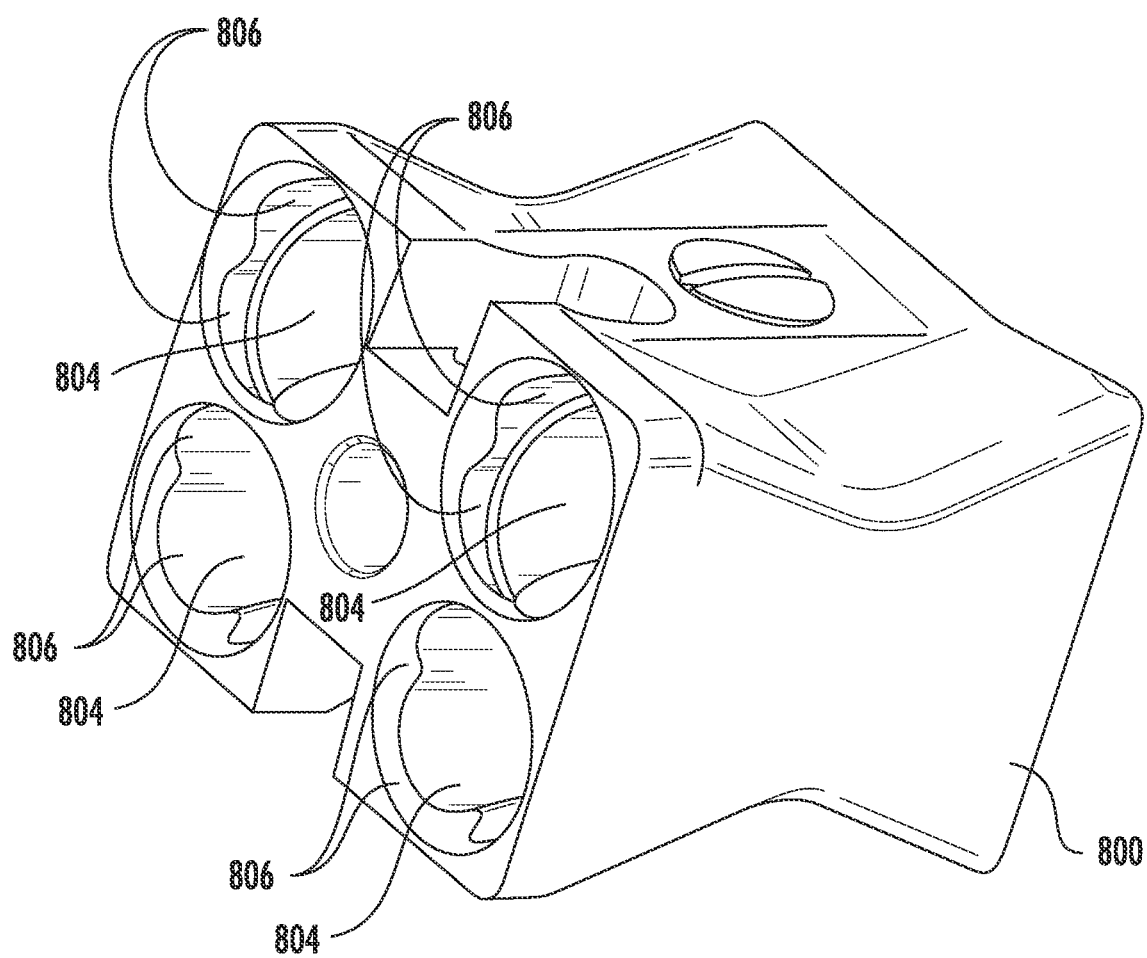
Figure 18:
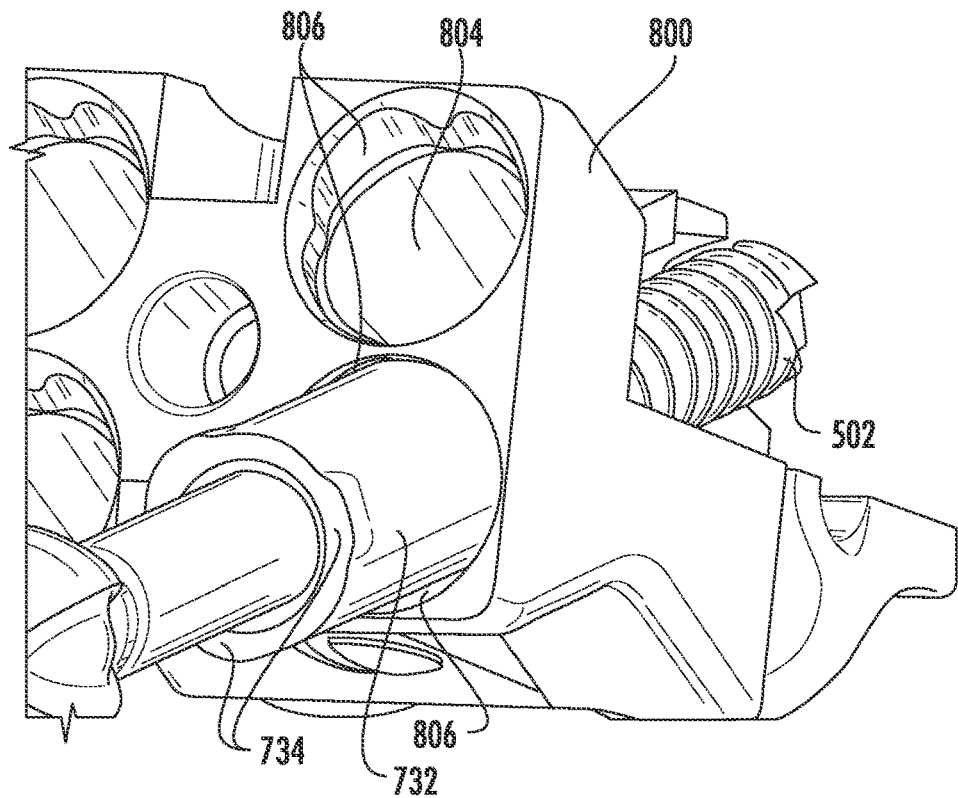
Figure 19:
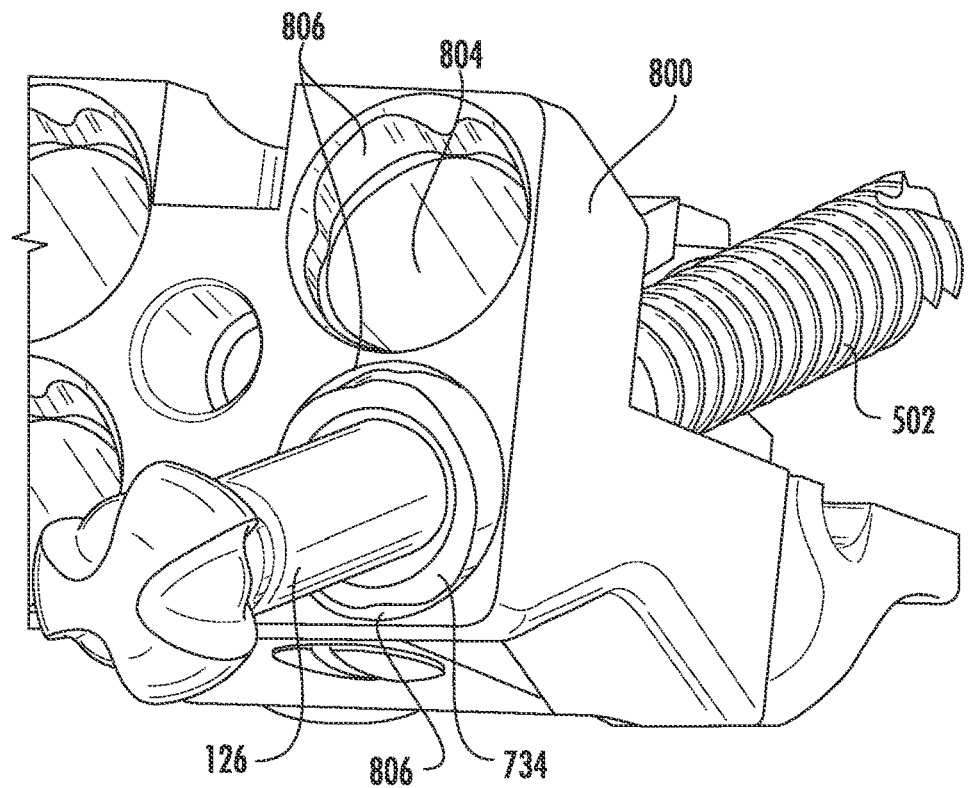

As shown in FIG. 19, the distal movement will cause the lobes 734 of the bushing 732 to be received within the lobes 802. As illustrated in FIGS. 13 and 17, the lobes 734 and the lobes 802 may be formed having complementary shapes such that the lobes 734 are received with the complementary shaped lobes 802. Engagement of the lobes 734 and lobes 802 will cause the bushing 732 to cease rotational and longitudinal movement (i.e., it will be stopped within the aiming hole 804).

Figure 20:
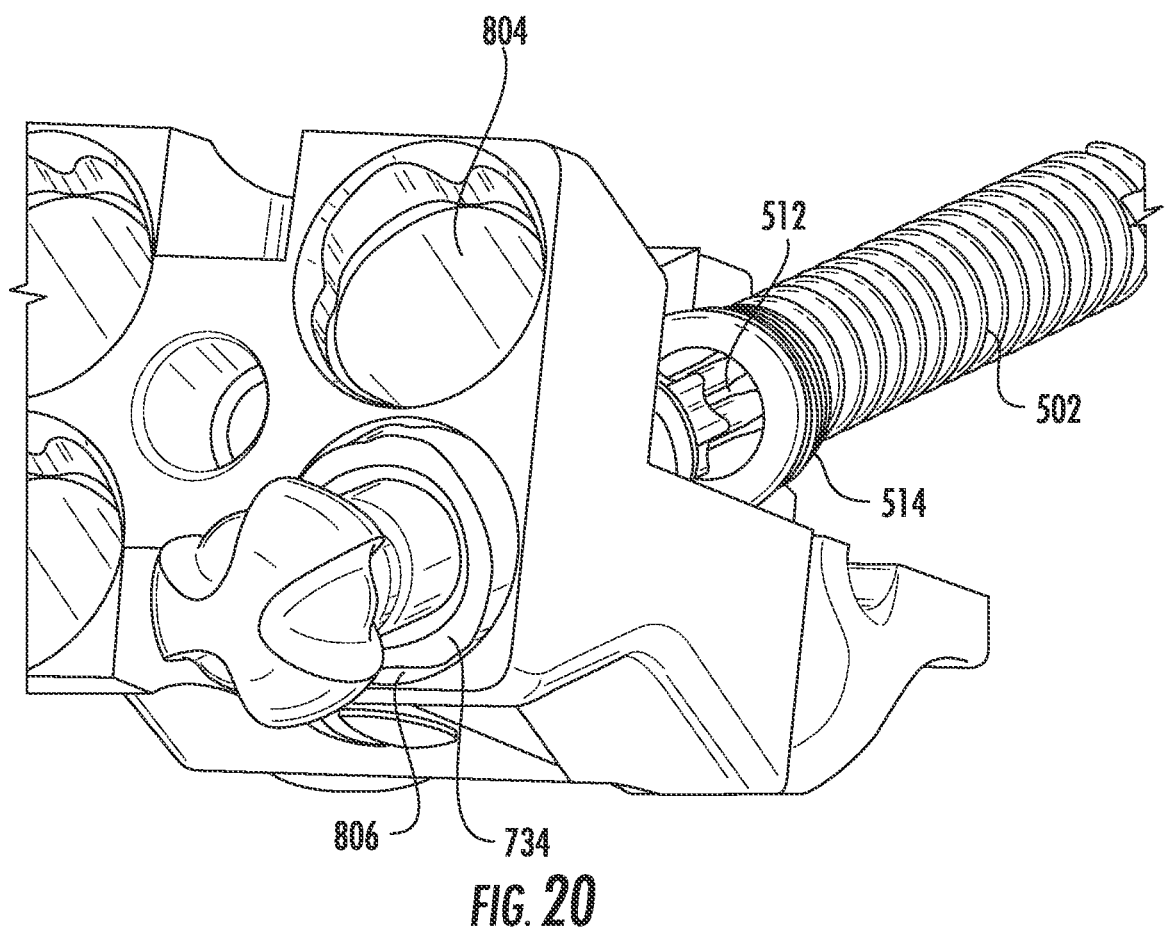

After the bushing 732 is stopped, the application of torque to the driver tip 126 will continue to rotate the screw 502 within the bushing 732. Thus, the screw 502 will continue to be driving in the distal direction along the longitudinal axis of the driver 100. As shown in FIG. 20, continuing to drive the screw 502 will rotate the threaded region 514 within the inner threads 506, causing the threaded region 514 to progress out of the distal end of the bushing 732. As such, the screw 502 advances from the bushing 732 and will be released from the driver 100. Operation of the articulating driver 100 may continue in order to drive the screw 502 into its final position through the continued engagement of the screw interface 512 with the head of the screw 502. Once the screw 502 reaches its final position, the articulating driver 100 may be withdrawn from the aiming device or guide 800.

Figure 21:
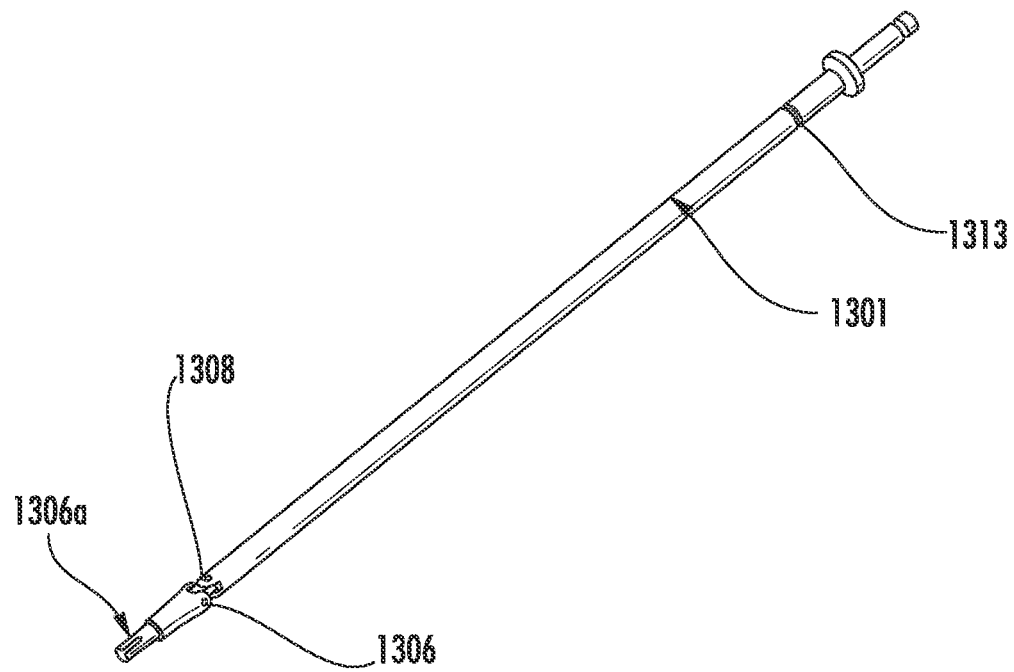
FIGS. 21-25 illustrate another embodiment of the driver device of the present disclosure.
Figure 22:
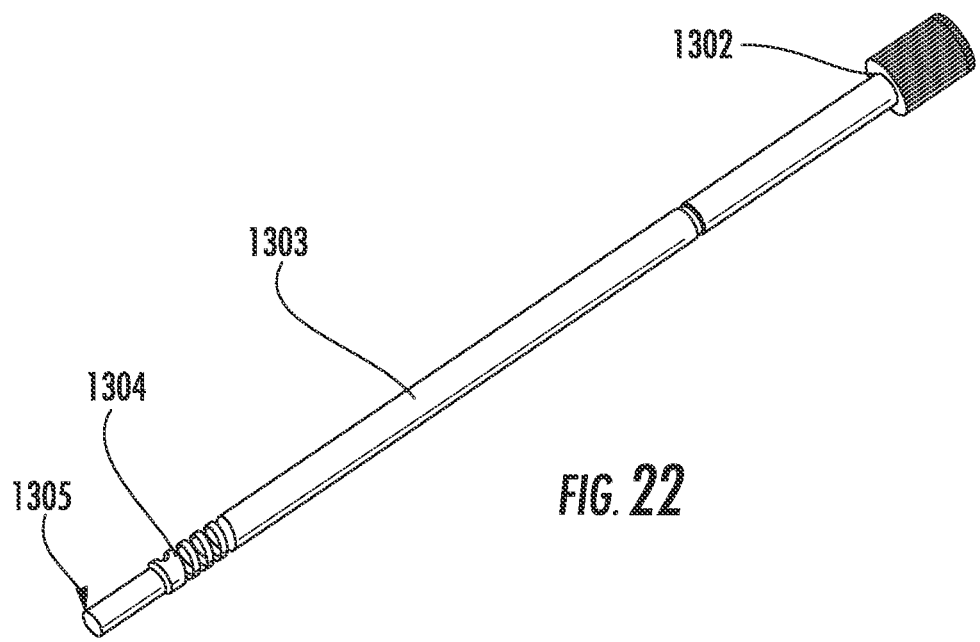
Figure 23:
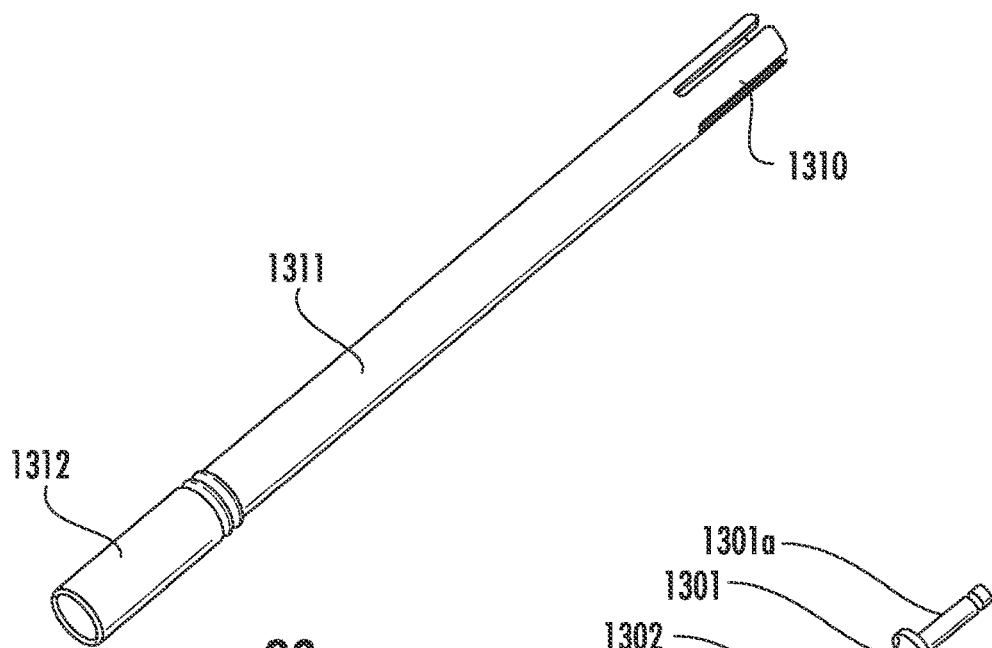
Figure 24A:
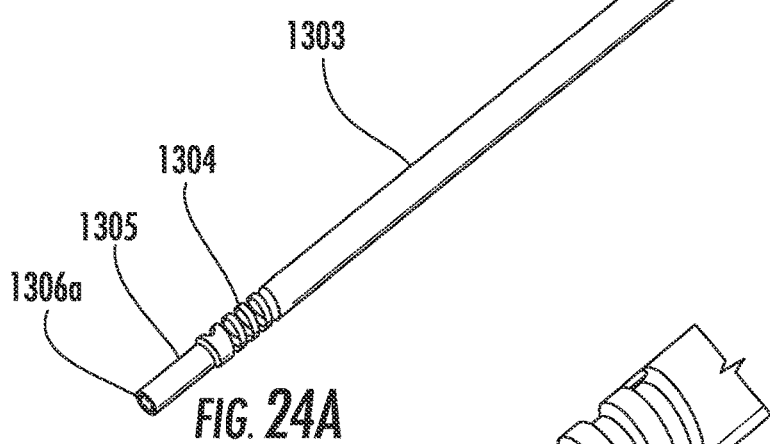
Figure 24B:
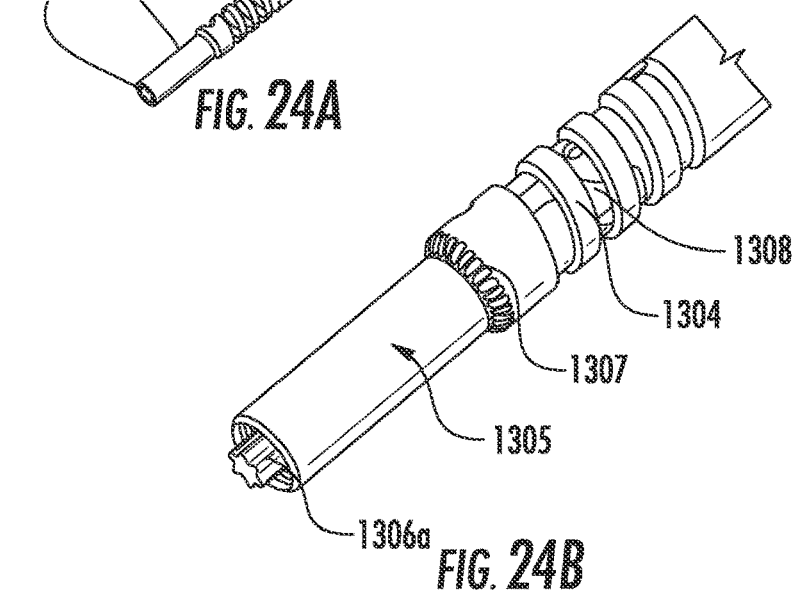
Figure 25:
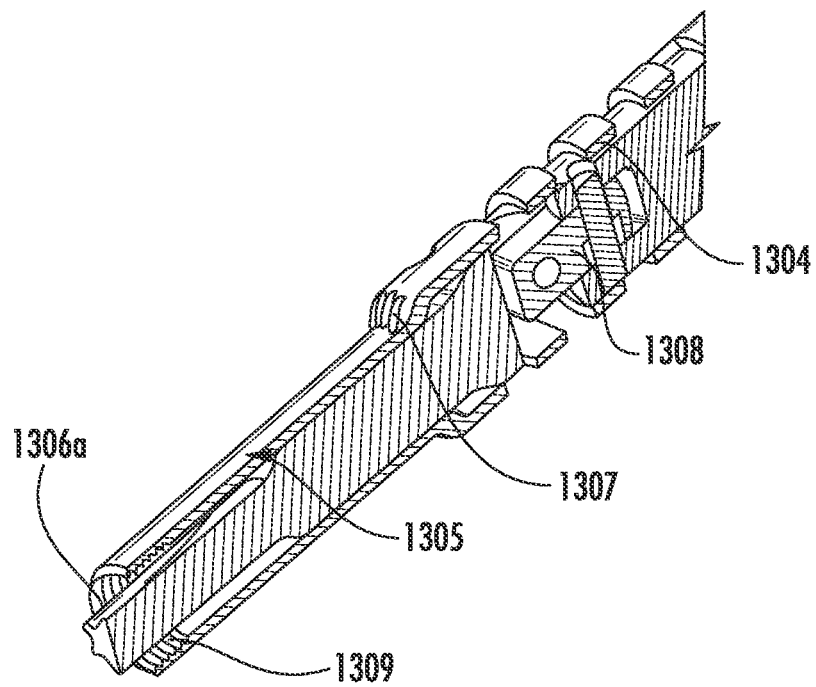

FIGS. 21-25 illustrate another embodiment of an articulating driver 1300 of the present disclosure. As shown, the articulating driver 1300 may include three components, a central screwdriver (FIG. 21), a central sleeve (FIG. 22) and an outer, slip sleeve (FIG. 23). The central screwdriver 1301 may be a straight or jointed driver. As illustrated in FIGS. 24A and 24B, the central screwdriver may be a jointed driver which is composed of a proximal shaft 1301 which has an interface 1301a that is adapted to provide a connection to, e.g., a handle for applying torque. The central screwdriver may include a jointed feature (e.g., a universal joint 1308) and a distal portion containing the screw interface 1306a (e.g., a self retaining star-drive). Alternatively, the joint mechanism 1308 may accomplished by beam coupling, spring coupling, jaw coupling, etc. Alternatively, the screw interface 1306a may have a hexagonal, square, polygonal shape, etc. The central screwdriver may include a distal tip 1306 that at a proximal end thereof, includes a circumferential groove 1313 to allow for retention of the central sleeve.

Referring now to FIG. 22, the central sleeve may include a mechanism 1302 to retain the central sleeve on the central screwdriver of FIG. 21. For example, the mechanism 1302 may be a spring-loaded quick coupling with detents for retention on the circumferential groove of the central screwdriver. Between the proximal end and the distal tip, there is a helical structure 1304 that may be provided to allow for bending of the jointed segment 1308 when the central sleeve is assembled. The nature of the helical structure 1034 allows it to act as a spring and hence bend with the joint segment 1038. The helical structure 1304 may be manufactured from a single solid tube with the central sleeve or may be bonded to the proximal and distal portion as a separate element. The later alternative would enable the use of any material that would be appropriate for the helical structure 1304. Such materials could be, but are not limited to, Nitinol, spring steel, certain grades of stainless steel or any other material which offers appropriate elasticity/memory. An additional benefit of the helical structure 1304 and its associated memory is that it prevents the loosening of jointed instruments, which is often encountered when there is repeated use of jointed instruments with universal joints.

At the distal tip of the central sleeve, a distal portion 1305 is providing having an outer diameter and length so as to have an appropriate interface with an aiming device or guide (e.g., 600) which may be used in association with the driver. An internal thread at the distal tip 1309 (FIG. 25) may engage the screw which would have to have either a straight or conical thread on the external surface of its head. The pitch of this internal thread would be optimized to match that of the thread on the screw.

To assemble the screw to the driver, the screw interface 1306*a* may protrude slightly out of the tip of the central sleeve. The screw would engage the screw interface 1306*a* of the driver, which may be a self-retaining interface. Then, using the retention mechanism 1032 of the central sleeve to act also as a turning knob, the central sleeve is turned such that the internal thread 1309 engages the external thread of the screw head. In turning this central sleeve, one or both of the following may occur, the screw is pulled further onto the screw driver interface 1306*a* or the helical structure 1304 elongates as the internal thread advances 1309 over the screw head. The screw is then rigidly fixed to the screwdriver via the threaded connection to the central sleeve and the connection of the central sleeve to the central driver. The screw is also connected to the central driver via the screw interface 1306*a* which allows for torque transmission and screw placement.

As the operator advances the screw, there may be a tendency to hold the length of the driver for guidance. If this holding occurs on the central sleeve, it may result in early disengagement of the screw from the central sleeve as the central sleeve would remain stationary relative to a rotating screw driver and screw. In order to prevent this from occurring, an outer slip sleeve 1311 may be positioned on the outside of the central sleeve. This slip sleeve 1311 may freely rotate about the central sleeve due to a non rigid connection 1310. This connection 1310 allows for rotation, but restricts translation. In addition, at the distal end of the slip sleeve, there is located a flexible plastic sleeve 1312 that covers the helical portion from entangling surrounding tissue.

As the screw nears its final position, the thread on its head engages an associated plate or portion of bone. However, in the insertion position, this head is covered by the central sleeve. Here, the user knows when to disengage the central sleeve. An alternative method involves the placement of toothed features 1307 on the distal portion of the central sleeve, which when approaching the final position, will engage into a counter-feature or the bone and will result in fixing the central sleeve from rotating with the central driver. Further rotation of the central driver will result in automatic disengagement of the screw from the central sleeve. The helical structure will allow the central sleeve can collapse with the advancement while the screwdriver-screw interface remains for optimum torque transmission. Once, the screw has been tightened into place, it will be no longer be connected to the driver itself and the driver is free to be removed.

In some implementations, in order to prevent deformation of the helical structure through over tightening of the central sleeve onto the screw, the helical structure may spiral in the opposite direction of the thread (i.e., counter-clockwise helical structure is provided for a clockwise thread). Therefore, over tightening will result in the helical structure collapsing onto the inner screwdriver and hence preventing it from deforming outward.

Figure 26:
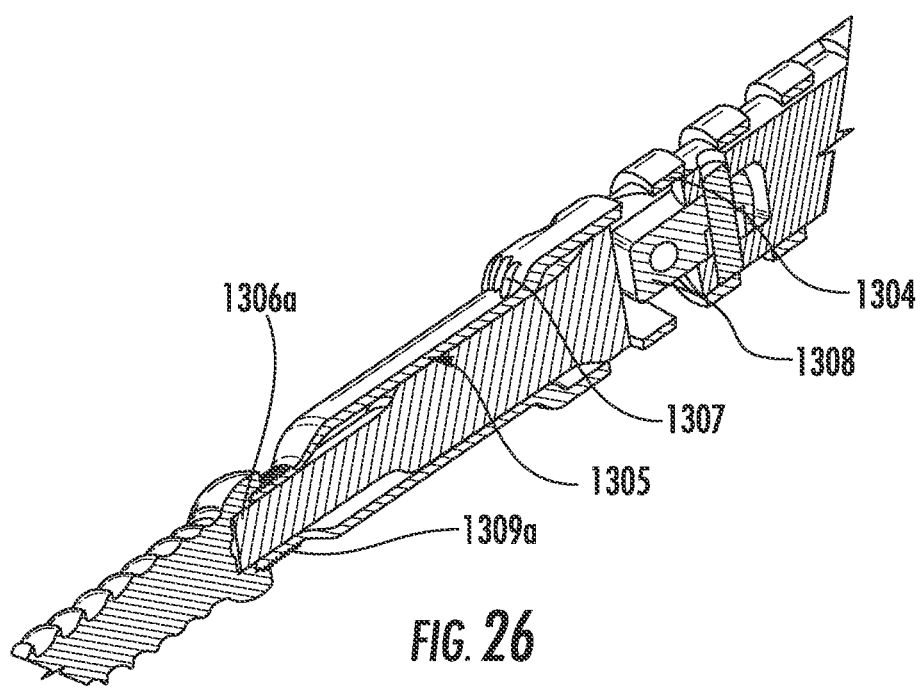
FIG. 26 illustrates another embodiment of the driver device of the present disclosure.

FIG. 26 illustrates another embodiment that uses an external thread on the central sleeve which would mate to a corresponding internal thread on the screw. Such a configuration may be used with variable angle screws or pedicle screws, and screws with locking threads.

In yet another embodiment, the design of FIGS. 21-25 may omit the toothed feature 1307. Turning of the screw with the head covered will result in engagement of the central sleeve onto the aiming device. Subsequent turning of the screw after this condition is achieved will result in lagging of the plate to the bone into which the screw is purchased or vice-versa.

FIGS. 27-31 illustrate another embodiment of a joint 2702 of the articulating driver of the present disclosure. As shown in FIGS. 27A-27C, the articulating driver 2700 consists of an input shaft 2704 that, at a first end 2706, connects to a handle (not shown) and has a first spherical head 2708. The first spherical head 2708 is secured within an articulation housing assembly 2710 by a first pin 2712 that passes through a cavity 2709. The input shaft 2704 may be any type of shaft capable of transmitting input torque from the handle or a power tool to which the input shaft 2704 is attached. A second spherical head 2724 is formed at a proximal end of a driver tip 2726 and is secured to the articulation housing assembly 2710 by a second pin 2734 that passes through a cavity 2729. When secured within the articulation housing assembly 2710, a ball 2718 formed at the distal end of the first spherical head 2708 is received within a socket 2722 that is defined within a proximal end of the second spherical head 2724, the interaction of the various components is described further with reference to FIG. 31.

Figure 27A:
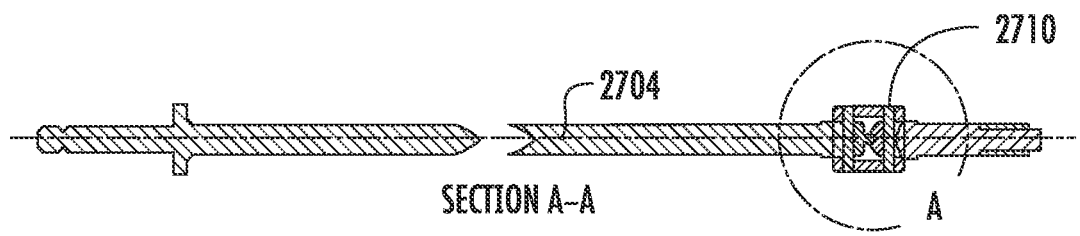
FIGS. 27A-27C illustrate another embodiment of the articulating driver of the present disclosure.
Figure 27B:
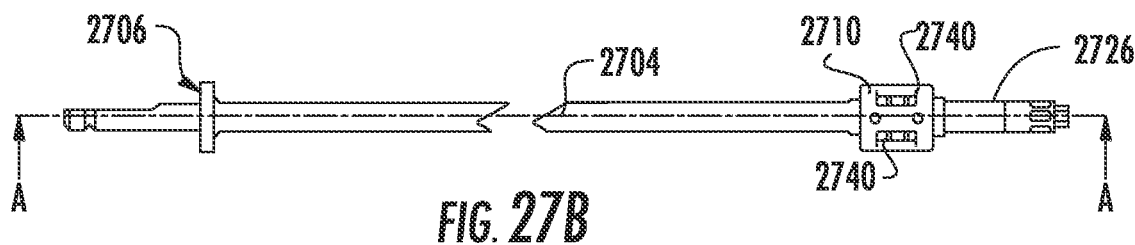
Figure 27C:
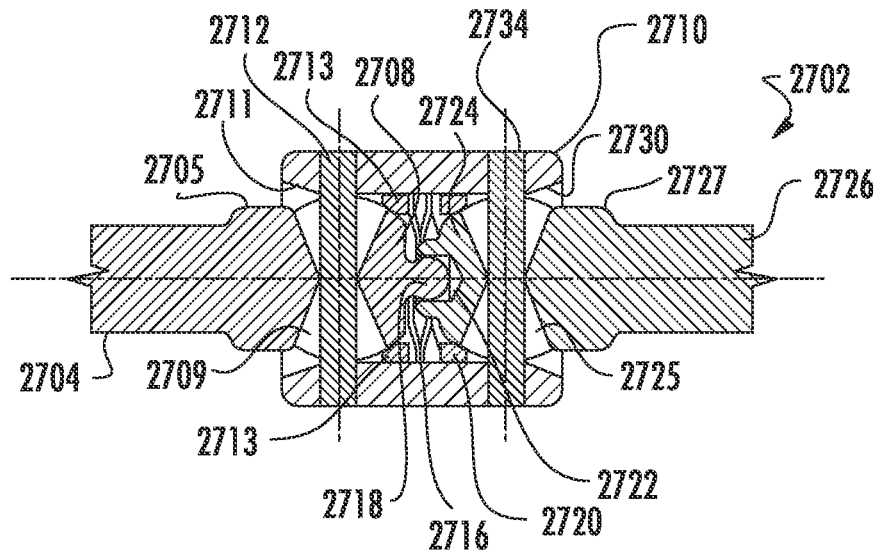

As shown in FIG. 27C, enclosed within the articulation housing assembly 2710 is the first spherical head 2708 of the input shaft 2704, a first washer 2712, a spring 2716, a second washer 2720, and spherical head 2724 of the driver tip 2726. The spring 2716 is disposed between a first washer 2714 and a second washer 2720. The first washer 2714 has a tapered edge that abuts the first spherical head 2708 and the second washer 2720 has a tapered edge that abuts the second spherical head 2734. The spring 2716 exerts an expansion force on both the first washer 2714 and the second washer 2720 to frictionally positionally retain the first spherical head 2708 and the second spherical head 2734 within the housing assembly 2710 a user-set angulation. The proximal and distal openings of the articulation housing assembly 2710 each have a chamfered edge 2711 and 2730, respectively, that are adapted to abut a first base 2705 and a second base 2727 to act as a stop to limit the total angulation of the joint 2702, as described below.

Figure 28A:
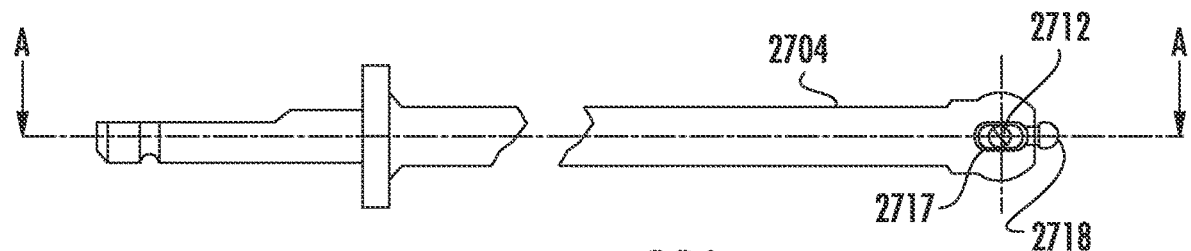
FIGS. 28A-28C illustrate a first spherical head of the embodiment of FIGS. 27A-27C.
Figure 28B:
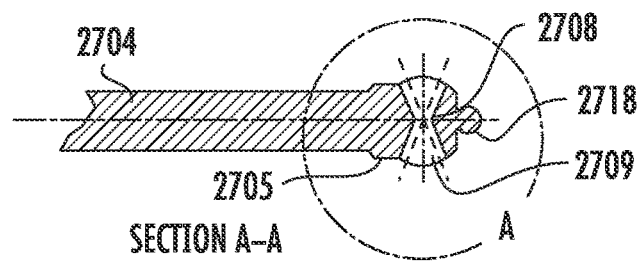
Figure 28C:
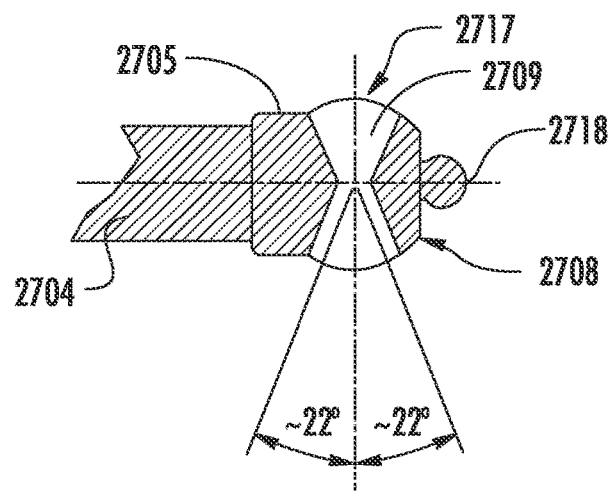

FIGS. 28A-28C illustrate the first spherical head 2708 in greater detail. As shown in FIG. 28A, the cavity 2709 forms a generally ovular opening 2717 on a surface of the first spherical head 2708 (a bottom opening is not shown in the FIGS.). In some implementations, the cavity 2709 may be milled into first spherical head 2708 having a generally "bow-tie" shape. As shown in the cross-sectional view of FIG. 28C, the cavity 2709 may be formed such the opening 2717 extends having an approximately 22° arc in each direction with respect to a center axis of the cavity 2709 (providing a total arc of approximately 44° across the surface of the first spherical head 2708). The "bow-tie" shaped of the cavity 2709 enables the first spherical head 2708 to be angulated with respect to the first pin 2712 passing therethrough, which can be appreciated is positioned along the center axis of the cavity 2709 shown in FIG. 28C when the first spherical head 2708 is assembled into the joint 2702.

Figure 29A:
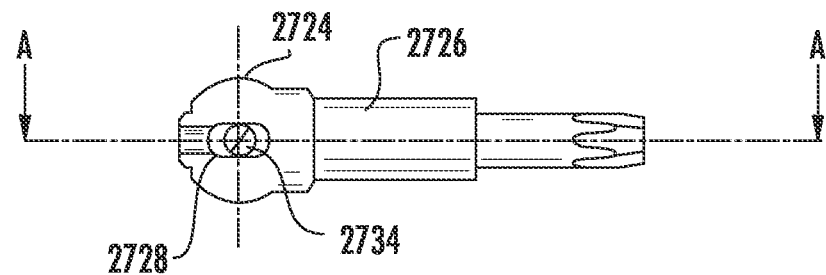
FIGS. 29A-29C illustrate a second spherical head of the embodiment of FIGS. 27A-27C.
Figure 29B:
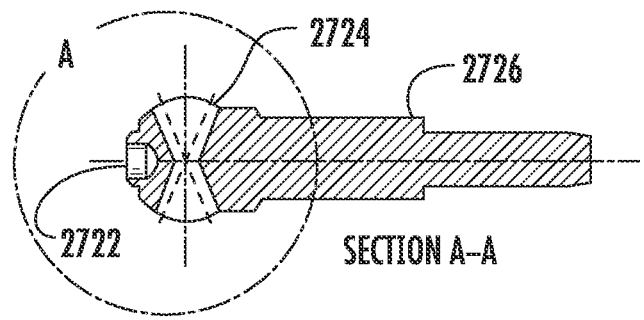
Figure 29C:
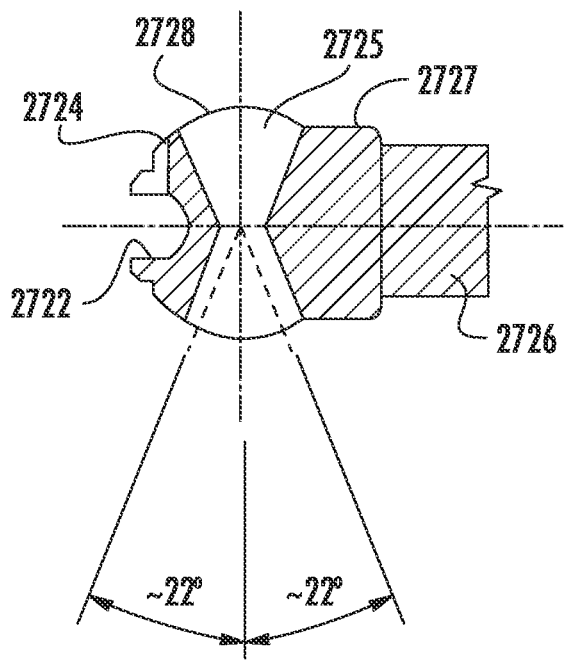

FIGS. 29A-29C illustrate the second spherical head 2724 in greater detail. As shown in FIG. 29A, the cavity 2725 forms a generally ovular opening 2728 on the surface of the second spherical head 2724 (a bottom opening is not shown of the FIGS.). In some implementations, the cavity 2725 may be milled into second spherical head 2724 having a "bow-tie" shape similar to the cavity 2709. As shown in the cross-sectional view of FIG. 29C, the cavity 2725 may be formed such the opening 2728 extends in a 22° arc in each direction with respect to a center axis of the cavity 2725. Thus, similar to the cavity 2709, the "bow-tie" shaped cavity 2725 enables the second spherical head 2724 to be angulated with respect to the second pin 2734, which can be appreciated is positioned along the center axis of the cavity 2725 shown in FIG. 29C when the second spherical head is assembled into the joint 2702.

Figure 30A:
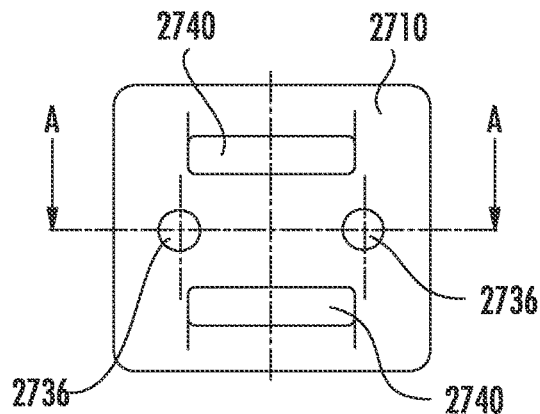
FIGS. 30A-30B illustrate the articulation housing assembly of the embodiment of FIGS. 27A-27C in greater detail.
Figure 30B:
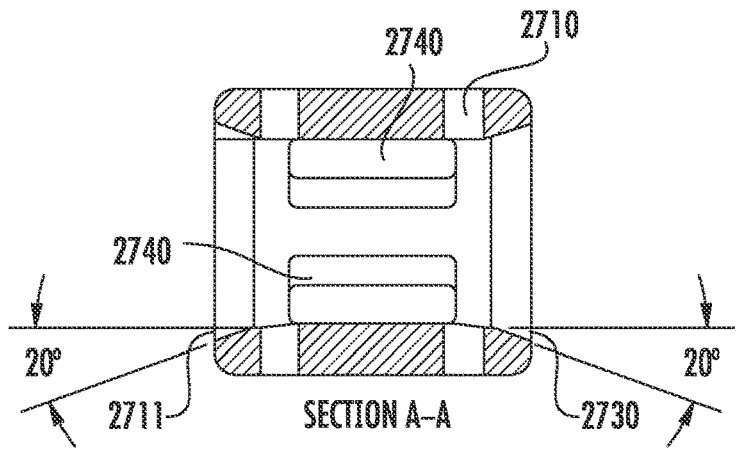

As shown in FIG. 30A-30B, the articulation housing assembly 2710 defines holes 2736 into which the first pin 2712 and the second pin 2734 may be pressed. Openings 2740 are provided to enable easy cleaning of the interior of the articulating housing assembly 2710. FIG. 30B illustrates the chamfered edges 2711 and 2730 of the proximal and distal openings of the articulation housing assembly 2710. Each edge may be formed having approximately a 20° angle with respect to the longitudinal axis of the articulation housing assembly 2710. The chamfered edges 2711 and 2730 may abut the first base 2705 and the second base 2727 to limit the total angulation at approximately 40°.

Figure 31:
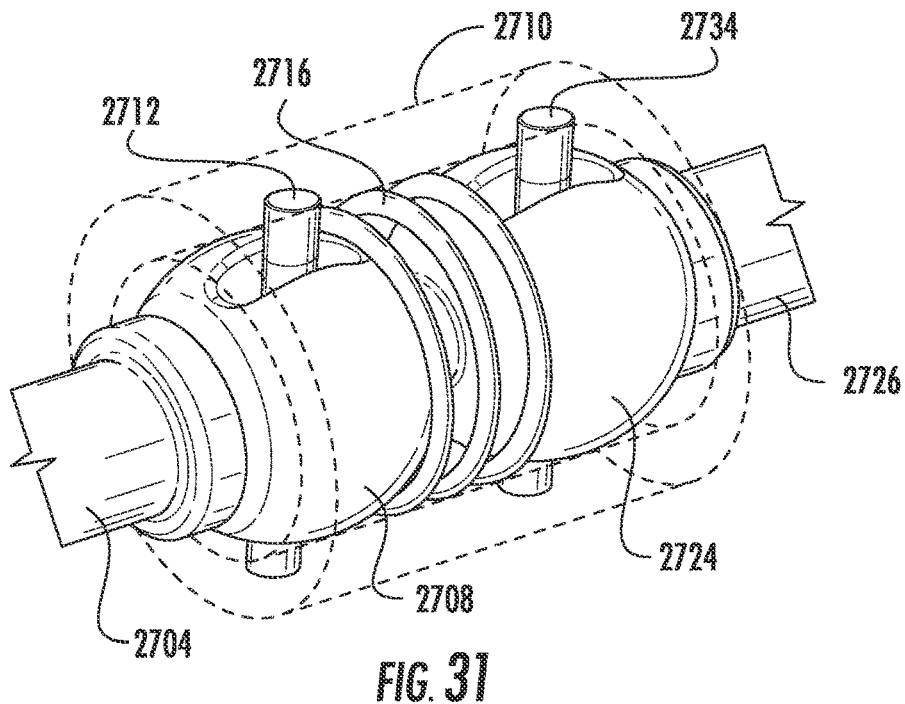
FIG. 31 illustrates a perspective view of the embodiment of FIGS. 27A-27C.

FIG. 31 illustrates a perspective view of the assembled joint 1702. To assemble the joint 1702, the input shaft 2704 is inserted into the articulation housing assembly 2710 and pinned to the articulation housing assembly 2710 by the first pin 2712. The first washer 2712, the spring 2716 and the second washer 2720 are then placed within the articulation housing assembly 2710. The driver tip 2726 is inserted into the articulation housing assembly 2710 and pinned by the second pin 2734. The pins 2712 and 2734 may be pressed-in and retained by an interference fit with the articulating housing 2710; the pins 2712 and 2734 may be welded in place, or may be threaded into articulating housing 2710. Other attachment mechanisms may be used in place of the pins 2712 and 2734.

The various components above may be made from stainless steel, titanium, titanium alloy, ceramic, etc. The first washer 2712 and the second washer 2720 may be made from PEEK. The spring 2716 may be any spring having a spring constant to exert a sufficient force on the first washer 2712 and the second washer 2720 to provide the aforementioned positional retention of the first spherical head 2708 and the second spherical head 2724 within the articulating housing 2710.

During use, a user can initially position the input shaft 2704 and the driver tip 2726 by angulating the input shaft 2704 and the driver tip 2726 to a desired total angulation. The approximately 22° of angulation of the first spherical head 2708 and the approximately 22° of angulation of the second spherical head 2724 may provide for a total angulation of approximately 44° of the driver tip 2726 with respect to the input shaft 2704. However, as noted above, the total angulation may be limited to approximately 40° by the interaction of the chamfered edges 2711 and 2730 and the first base 2705 and the second base 2727. The angulation may be maintained throughout a 360 rotation of the input shaft 2704 and driver tip 2726 by the positional retention provided by the interaction of the spring 2716, the first washer 2714 and the second washer 2720 and the constant velocity provided by the ball 2718 and the socket 2722.

As the user rotates the input shaft 2704, torque is transmitted to the articulation housing assembly 2710 via the interaction of the first pin 2712 within the cavity 2709 of the first spherical head 2708. This torque is then transmitted from the articulation housing assembly 2710 to the driver tip via action of the second pin 2734 within the cavity 2725 of the second spherical head 2724 of the driver tip 2726. The driver tip 2726 then transmits the torque to the attachment to turn, e.g., screws for insertion into bone.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A driver having a ball-in-socket joint, comprising:
a driver tip having a spherical head;
a retention cap having a domed surface to mate with the spherical head;
an input shaft;
a spring disposed in an end of the input shaft and in a recess of the retention cap opposite that of the domed surface; and
a housing that receives the input shaft, the spring, the retention cap and the spherical head,
wherein the housing has a tapered end to positionally retain the spherical head therein, and
wherein the spherical head has a plurality of grooves defined in a surface thereof, the housing defines a plurality of holes, and each of the holes receives a pin that passes through the housing and is received within a respective groove of the spherical head, and
wherein torque applied at the input shaft is transmitted to the housing and to the driver tip by action of the pins within the grooves of the spherical head.

2. The driver of claim 1, wherein the plurality of grooves have a shape to provide for up to 50° of angulation of the driver tip with respect to the input shaft over a 360° rotation of the input shaft.

3. The driver of claim 2, wherein the grooves have a generally ovular shape and a W-shape cross-section within the spherical head.

4. The driver of claim 1, wherein the grooves are positioned within the spherical head at offsets of approximately 120°.

5. The driver of claim 1, wherein the grooves extend over an approximately 120° arc across a face of the spherical head.

6. The driver of claim 1, wherein the spring exerts a force on the retention cap to positionally retain the spherical head within the housing.

7. The driver of claim 1, wherein the driver can be a jointed awl, a screw driver or a drill.

8. The driver of claim 1, wherein one end of the spring is received within a cavity in the end of the input shaft.

9. The driver of claim 1, wherein the retention cap transmits force from the spring to the spherical head of the driver tip.

10. The driver of claim 1, wherein the spherical head transmits torque to an attachment that is received within a bushing, and wherein the attachment is provided on an outer surface of the driver tip axially spaced from the spherical head.

11. The driver of claim 10, wherein the bushing provides positional retention of the attachment.

12. The driver of claim 10, wherein the bushing is made of polyester ether ketone (PEEK).

13. The driver of claim 1, wherein a radius of the tapered end of the housing decreases to conform to the spherical head of the driver tip.

14. The driver of claim 1, wherein the input shaft is coupled to the housing with a cross-pin.

15. The driver of claim 14, wherein the cross-pin can be pressed-in, welded in place, threaded into the input shaft, or retained within a sleeve, the sleeve configured to prevent the cross-pin from backing out.

16. The driver of claim 1, wherein the retention cap can be fabricated from PEEK, stainless steel, or polyethylene.

17. The driver of claim 16, wherein the retention cap comprises a titanium nitride (TiN) coating configured to limit wear on the spherical head.

18. A driver having a ball-in-socket joint, comprising:
a driver tip having a spherical head;
a retention cap having a domed surface to mate with the spherical head;
an input shaft;
a spring disposed in an end of the input shaft and in a recess of the retention cap opposite that of the domed surface; and
a housing that receives the input shaft, the spring, the retention cap and the spherical head, wherein the input shaft is coupled to the housing with a cross-pin that extends into the input shaft,
wherein the housing has a tapered end to positionally retain the spherical head therein.

19. The driver of claim 18, wherein the cross-pin can be pressed-in, welded in place, threaded into the input shaft, or retained within a sleeve, the sleeve configured to prevent the cross-pin from backing out.

20. The driver of claim 18, wherein torque applied at the input shaft is transmitted to the housing and to the driver tip by action of pins received within grooves of the spherical head.

* * * * *